(12) United States Patent
Weaver et al.

(10) Patent No.: US 10,617,809 B2
(45) Date of Patent: Apr. 14, 2020

(54) ELECTRICAL SENSOR FOR FLUIDS

(71) Applicant: Fresenius Medical Care Holdings, Inc., Waltham, MA (US)

(72) Inventors: Colin Weaver, Pleasanton, CA (US); Elliott Alber, Pleasanton, CA (US); Philip Scott James, Orinda, CA (US); Daniel Schmidt, Petaluma, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/081,033

(22) PCT Filed: Dec. 29, 2016

(86) PCT No.: PCT/US2016/069298
§ 371 (c)(1),
(2) Date: Aug. 30, 2018

(87) PCT Pub. No.: WO2017/117442
PCT Pub. Date: Jul. 6, 2017

(65) Prior Publication Data
US 2019/0255240 A1 Aug. 22, 2019

(51) Int. Cl.
*A61M 1/16* (2006.01)
*G01N 27/07* (2006.01)

(52) U.S. Cl.
CPC ........ *A61M 1/1607* (2014.02); *A61M 1/1609* (2014.02); *A61M 1/1617* (2014.02);
(Continued)

(58) Field of Classification Search
CPC ... H05K 1/03; H05K 1/14; A61B 5/00; A61B 90/98; G01L 1/22
See application file for complete search history.

(56) References Cited

U.S. PATENT DOCUMENTS

| | | |
|---|---|---|
| 5,631,352 A | 5/1997 | Lauk |
| 5,644,240 A | 7/1997 | Brugger |
| (Continued) | | |

FOREIGN PATENT DOCUMENTS

| | | |
|---|---|---|
| WO | WO 2014/061777 A1 | 4/2014 |
| WO | WO 2015/011065 A1 | 1/2015 |

OTHER PUBLICATIONS

"HealthPACT: Emerging Health Technology, An Overview of Emerging Home Renal Dialysis Technologies Including Nx Stage," Health Policy Advisory Committee on Technology, State of Queensland, Australia (Aug. 2012).

(Continued)

*Primary Examiner* — Richard C Gurtowski
(74) *Attorney, Agent, or Firm* — Leydig, Voit & Mayer, Ltd.

(57) ABSTRACT

An electrical sensor for sensing electromagnetic properties of process fluids in a dialysis machine or a similar medical device can include a probe for interfacing with the fluids that is made from electronic fabric materials. The electronic fabric probe can include one or more conductors embedded in a non-conductive fabric layer. The electronic fabric probe is accommodated an enclosure which establishes a flow path with respect to the probe to establish fluid contact between the process fluids and the conductors. The conductors can apply or sense current and/or voltage with respect to the fluid. A portion of the electronic fabric probe can be disposed externally of the enclosure to provide electronic communication externally of the enclosure.

15 Claims, 13 Drawing Sheets

(52) U.S. Cl.
CPC ........ *A61M 1/1656* (2013.01); *A61M 1/1696* (2013.01); *G01N 27/07* (2013.01); *A61M 2205/3317* (2013.01); *A61M 2205/3334* (2013.01); *A61M 2205/3561* (2013.01); *A61M 2205/3592* (2013.01)

(56) References Cited

U.S. PATENT DOCUMENTS

| | | | |
|---|---|---|---|
| 5,744,027 | A | 4/1998 | Connell et al. |
| 6,110,384 | A | 8/2000 | Goux et al. |
| 6,139,754 | A | 10/2000 | Hartranft et al. |
| 7,682,328 | B2 * | 3/2010 | Han ................. A61M 1/3653 210/645 |
| 7,794,141 | B2 | 9/2010 | Perry et al. |
| 7,891,243 | B2 | 2/2011 | Winkens |
| 7,896,831 | B2 | 3/2011 | Sternby et al. |
| 7,959,594 | B2 | 6/2011 | Wariar et al. |
| 8,246,567 | B2 | 8/2012 | Bene |
| 8,366,655 | B2 | 2/2013 | Kamen et al. |
| 8,708,946 | B2 | 4/2014 | Han et al. |
| 8,741,147 | B2 | 6/2014 | Bene et al. |
| 8,764,987 | B2 | 7/2014 | Gross et al. |
| 8,792,089 | B2 | 7/2014 | Zhang et al. |
| 8,801,646 | B2 | 8/2014 | Han et al. |
| 8,828,232 | B2 | 9/2014 | Shah et al. |
| 8,834,401 | B2 | 9/2014 | Petisce et al. |
| 8,870,769 | B2 | 10/2014 | Deshpande |
| 8,880,371 | B2 | 11/2014 | Beyer et al. |
| 8,889,004 | B2 | 11/2014 | Updyke et al. |
| 8,894,600 | B2 | 11/2014 | Kelly et al. |
| 8,900,172 | B2 | 12/2014 | Pohlmeier |
| 8,906,240 | B2 | 12/2014 | Crnkovich |
| 8,973,424 | B2 | 3/2015 | Wiktor |
| 2003/0211797 | A1 * | 11/2003 | Hill ................. D03D 1/0088 442/205 |
| 2005/0082226 | A1 | 4/2005 | Bene et al. |
| 2005/0209563 | A1 | 9/2005 | Hopping et al. |
| 2007/0253463 | A1 | 11/2007 | Perry et al. |
| 2009/0007642 | A1 * | 1/2009 | Busby ................. A61M 1/28 73/61.44 |
| 2011/0189048 | A1 | 8/2011 | Curtis et al. |
| 2012/0010554 | A1 | 1/2012 | Vantard et al. |
| 2012/0068723 | A1 | 3/2012 | Sullivan |
| 2012/0101422 | A1 | 4/2012 | Muller |
| 2012/0206239 | A1 * | 8/2012 | Ikemoto ............ G06K 7/10346 340/10.1 |
| 2012/0232471 | A1 | 9/2012 | Chen et al. |
| 2012/0277552 | A1 | 11/2012 | Gerber |
| 2012/0277655 | A1 | 11/2012 | Gerber |
| 2013/0020237 | A1 | 1/2013 | Wilt et al. |
| 2013/0056419 | A1 | 3/2013 | Curtis |
| 2013/0131579 | A1 * | 5/2013 | Mantell ................. A61M 13/00 604/23 |
| 2013/0319920 | A1 | 12/2013 | Hansson et al. |
| 2014/0060161 | A1 * | 3/2014 | Schick ................. G01N 37/00 73/53.01 |
| 2014/0158538 | A1 | 6/2014 | Collier et al. |
| 2014/0158623 | A1 | 6/2014 | Pudil et al. |
| 2014/0190876 | A1 | 7/2014 | Meyer et al. |
| 2014/0190886 | A1 * | 7/2014 | Pudil ................. A61M 1/28 210/632 |
| 2014/0190891 | A1 | 7/2014 | Lura et al. |
| 2014/0220699 | A1 | 8/2014 | Pudil et al. |
| 2014/0238909 | A1 | 8/2014 | Brugger et al. |
| 2014/0316297 | A1 | 10/2014 | McCaughan et al. |
| 2014/0326646 | A1 | 11/2014 | Strohhoefer et al. |
| 2015/0005699 | A1 | 1/2015 | Burbank et al. |
| 2015/0008183 | A1 | 1/2015 | Crnkovich et al. |
| 2015/0042366 | A1 | 2/2015 | Wilt et al. |
| 2015/0076044 | A1 | 3/2015 | Kelly et al. |
| 2015/0080782 | A1 | 3/2015 | Roger et al. |
| 2015/0088047 | A1 | 3/2015 | Gerber et al. |
| 2019/0056277 | A1 * | 2/2019 | Ronay ................. G01L 1/2212 |
| 2019/0192022 | A1 * | 6/2019 | Ram ................. A61B 7/00 |

OTHER PUBLICATIONS

Sam, Ramin, "Hemodialysis: Diffusion and Ultrafiltration," *Austin J. of Nephrology and Hypertension*, 1(2) (2014).

International Patent Application No. PCT/US2016/069298, International Search Report (dated Mar. 20, 2017).

* cited by examiner

ELECTRICAL SENSOR FOR FLUIDS

CROSS-REFERENCE TO RELATED APPLICATIONS

This application is a U.S. National Phase application under 35 U.S.C. § 371 of International Application No. PCT/US2016/069298, filed on Dec. 29, 2016, and claims benefit to U.S. application Ser. No. 14/982,805, filed on Dec. 29, 2015, both of which are incorporated herein by reference in their entireties.

BACKGROUND OF THE DISCLOSURE

Hemodialysis is a medical procedure performed to treat patients suffering from renal failure, kidney problems or other related conditions in which the kidneys are unable to adequately remove impurities and waste products from the patient's blood. In the hemodialysis process, a dialysis system or dialysis machine removes blood from the patient's body and directs it through a filtration device referred to as a dialyzer that filters the cleaned blood for return to the patient. The filtration process is performed by directing a liquid solution, often referred to as a dialysate, through the dialyzer, and which is separated from the blood therein by a membrane so that waste products are drawn or diffuse into the dialysate. To facilitate treatment of different patients with different conditions, the composition of the dialysate may be adjusted or regulated by the dialysis machine during the dialysis process, for example, by introducing different additives to the solution to adjust its characteristics.

To facilitate the preparation and adjustment of the dialysate solution, various sensors and controls are incorporated into the dialysis machine to monitor the preparation process and the composition of the dialysate solution. Using these sensors and controls, the dialysis machine can be designed to automatically make adjustments during the dialysis treatment, or a health care technician monitoring the sensors and controls can make the necessary adjustments. The sensors and controls may therefore play a significant role during the dialysis treatment. However, because the dialysis process necessarily involves human biological substances, the sensors and controls must be incorporated into the dialysis machine in a manner to isolate them or to enable their cleansing and/or sterilization. The present disclosure is directed to supplementing and improving the operation and functionality of the sensors and controls associated with a dialysis machine or similar medical device.

BRIEF SUMMARY OF THE DISCLOSURE

The disclosure provides an electrical or electromechanical sensor for analyzing process fluids in a dialysis machine or similar medical device by measuring or sensing certain electromagnetic properties associated with the fluid. To directly interface with the fluid, the electrical or electromechanical sensor can utilize an electronic fabric probe having conductive properties that is made of a pliable, non-conductive fabric layer with one or more electrical conductors attached thereto in an exposed manner. The conductors may be attached to the fabric layer by weaving, stitching, carding, matting, or other appropriate methods. Electronic fabrics of this type may also be referred to as electronic textiles or smart fabrics. The electronic fabric probe can be cut or trimmed to shape and disposed inside a non-conductive enclosure that defines a fluid chamber. Process fluids can be directed into the fluid chamber to electrically contact the exposed conductors of the electronic fabric probe. Accordingly, voltage and/or current can be applied to the process fluid in the fluid chamber through use of the conductors in the electronic fabric probe. To establish electrical communication with the conductors, a portion of the electronic fabric probe can extend externally of the enclosure. In an embodiment, the enclosure can be formed of molded plastic or the like and can be readily disassembled to enable removal of the electronic fabric probe.

A possible advantage is the disclosure provides an electrical sensor that can detect electromagnetic properties such as, for example, the characteristics of an electromagnetic field, which are associated with a process fluid in a dialysis machine or similar device through the use of conductive electronic fabrics. The electronic fabric probe may be cut from a larger swath of the electronic fabric material thereby providing a unique manufacturing benefit associated with the disclosure. Another possible advantage is that because the enclosure can be made of a low cost molded plastic and readily disassembled, the electrical sensor can be readily removed from the dialysis machine and either discarded in its entirety, or the electronic fabric probe can be removed from the enclosure and replaced. This advantage can be readily appreciated given the electrical sensor's exposure to potentially biohazardous process fluids.

In another aspect, the disclosure describes various uses of an electronic fabric probe to measure different properties of a fluid in a fluid circuit such as flow rate or fluid pressure. The electrode conductors embedded in the non-conductive fabric layer can be arranged to measure these fluid properties based on electrical characteristics of the electronic fabric probe associated with the conductor arrangement. In another aspect, the arrangement of the conductors can provide an identification or verification feature conveying information about the electronic fabric probe, for example, to ensure it is the correct probe or correctly installed. In a further aspect, the electronic fabric probe can be configured to shield the electrode conductors from electromagnetic fields and the like. An advantage of these aspects of the disclosure is the use of inexpensive and disposable electronic fabrics for a variety of fluid measurements and sensor types. Further, the electronic fabric probes can be used as backup or diagnostic sensors to assist other sensor in the system. These and other advantages will become apparent from the following detailed description and the accompanying drawings.

DETAILED DESCRIPTION

Figure 1:
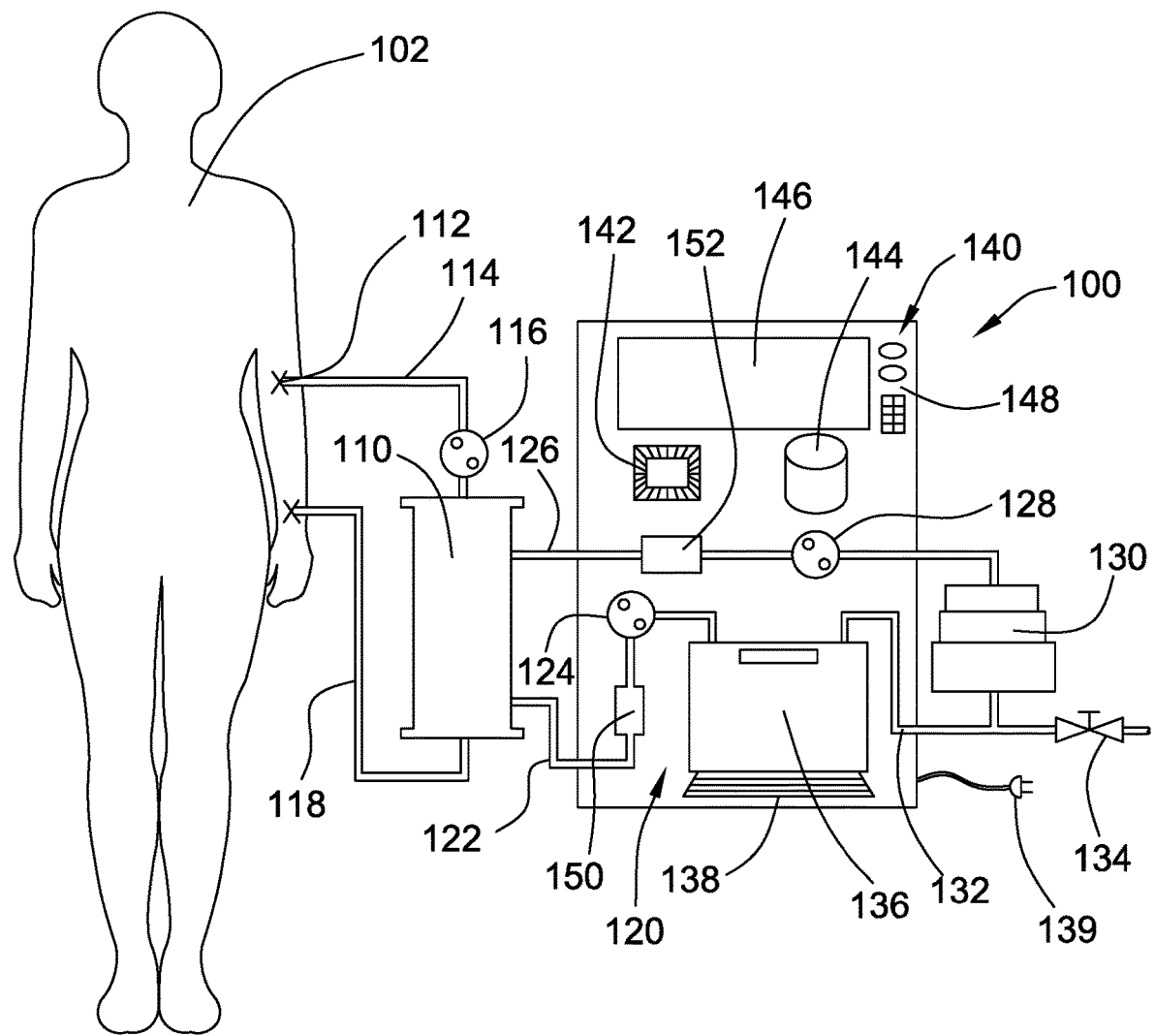
FIG. 1 is a front elevational schematic representation of a dialysis system for treating blood removed from a patient with dialysate fluid and that includes an electrical sensor for analysis of fluids utilized in the dialysis process.

Now referring to the drawings, wherein like reference numbers refer to like elements, there is illustrated in FIG. 1 a medical treatment system in the particular embodiment of a dialysis machine 100 for performing a hemodialysis treatment on a patient 102. It should be noted that although various aspects of the present disclosure are described with respect to hemodialysis treatment, these aspects may have application beyond hemodialysis treatment and are not intended to be specifically limited to hemodialysis, nor are the claims so limited unless explicitly stated. Furthermore, the illustrated dialysis machine may be intended for at-home use or portability outside of a medical clinic; however, aspects of the disclosure may be applicable to other configurations for dialysis treatment and the claims are not intended to be so limited unless explicitly stated therein. The dialysis machine 100 can be equipped with a dialyzer 110 in which the filtration of blood is performed. The dialyzer 110 can be a cross-flow dialyzer in which blood flowing in one direction is separated from a dialysate fluid flowing in the opposite direction by a semi-permeable membrane. During the dialysis process, solutes, fluids, and impurities in the blood can diffuse or transfer across the membrane to the dialysate to be directed out of the dialyzer 110. In various embodiments, the dialyzer 110 may be a single use device or may be configured for multiple uses.

To direct blood from the patient 102 to the dialyzer 110, a catheter 112 is inserted into the patient and can be connected to the dialysis machine 100 via tubing or a removal line 114. The catheter 112 may be temporarily inserted for the procedure or may be surgically grafted into the body of the patient 102. To maintain the flow of blood from the patient 102 to the dialyzer 110, a pump 116 such as a rotary peristaltic pump can be operatively associated with the dialyzer and can be disposed along the removal line 114 to apply a pressure to the lines that directs or supplements blood flow in the appropriate direction. Filtered blood from the dialyzer 110 is returned to the patient 102 via a return line 118.

To supply dialysate during the dialysis treatment, the dialysis machine 100 can be operatively associated with a dialysate system 120 that is configured to prepare and adjust the dialysate solution. In an embodiment, the dialysate system 120 can be a sorbent system in which the dialysate is reformulated and re-circulated by the dialysis machine 100 without a significant production of waste fluid, although in other embodiments, the dialysis machine can be a more conventional single pass system in which used dialysate must be stored in a suitable receptacle for eventual disposal. To introduce fresh dialysate to the dialyzer 110, the dialyzer can be disposed in fluid communication with the dialysate system 120 through a dialysate supply line 122, which may be a flexible hose or tubing of appropriate, medically suitable material. Disposed in line with the dialysate supply line 122 can be another peristaltic pump 124 that applies appropriate pressure to direct the dialysate solution through the dialyzer 110. After passing through the dialyzer 110 to treat the counter flowing blood, the used dialysate is returned to the dialysis machine 110 by a dialysate return line 126, which may be associated with a third peristaltic pump 128 to maintain flow of the dialysate solution.

To facilitate recycling and reconditioning of the used dialysate, the dialysate solution is directed by the dialysate return line 126 to a sorbent cartridge 130 where the fluid is cleaned and purified. The sorbent cartridge 130 can be a disposable unit made of a plurality of layers or segments of different elements and compounds that trap and remove impurities in the dialysate solution that were disposed therein from the blood during the dialysis process. The impurities remain in the sorbent cartridge 130 while the filtered dialysate is returned to the dialysis machine 100 via a sorbent return line 132. An advantage of the sorbent system is that it recycles much of the dialysate solution, including the purified reverse osmosis water initially utilized for the dialysate, while providing a convenient manner for disposing of the biological impurities removed from the patient's blood through the dialyzer 110. However, in various embodiments, the sorbent return line 132 can be in fluid communication with a reverse osmosis water supply 134 that can supplement the water content of the recycled solution if necessary.

To further recondition the solution returned from the sorbent cartridge 130, the dialysate system 120 can include a cassette or dialysate bag 136 disposed in the dialysis machine and which contains various additives and chemicals. The dialysate bag 136 may also include tubing or flow channels for directing the recycled solution into contact with the additives for incorporation and may further be compartmentalized to separate the additives. To facilitate adsorption of the additives into the recycled solution and to avoid cooling of the patient blood during the dialysis process, the dialysate bag 136 may be operatively associated with a heater 138. The quantities of the additives may be measured and intended for a single dialysis treatment process or, in other embodiments, they may be added to the recycled solution via appropriate metering equipment. In the single use embodiment, the dialysate bag 136 can be removed from the dialysis machine and replaced after use. In addition to the dialysate bag 136, the dialysate system 120 can include other sources of compounds and fluid solutions to formulate the dialysate and may be associated with meters and detectors to check for blood presence in the dialysate, quality levels, composition and formulation of the dialysate, may include de-aerators, etc. The freshly prepared dialysate is directed again to the dialyzer by the dialysate supply line 122. To provide electrical power for operation of the peristaltic pumps 124, 128 and the heater 138 as well as other equipment, the dialysis machine 100 can be operatively associated with a power source 139, such as a plug for an electrical outlet or, in other embodiments, a rechargeable battery pack.

To monitor and control the dialysis process, an electronic or computerized control unit, module, or controller 140 can be operatively associated with the dialysis machine 100. The controller 140 is adapted to monitor various operating parameters and to responsively regulate various variables and functions affecting the dialysate system 120 and the other systems of the dialysis machine 100. The controller 140 can include a microprocessor 142, an application specific integrated circuit (ASIC), or other appropriate circuitry, and can have memory 144 or other data storage capabilities on a computer readable medium. The microprocessor 142 and the memory 144 can be configured to store, retrieve, and execute programming instructions to conduct the dialysate formation and recycling process and adjustably respond to changes in the process as they arise. To enable a technician or operator to interface with the dialysis machine, the controller 140 can be operatively associated with a human-machine interface 146 such as a liquid crystal display device that may include touch screen capabilities. The human-machine interface 146 can display visual information regarding the dialysis process and the operational state of the dialysis machine 100 and can receive input from the operator through tactile capabilities. The controller 140 may be further associated with a physical control panel 148 that includes switches, knobs, keypads, and the like through which the operator may initiate and adjust the dialysis processes.

To monitor and analyze the composition, parameters, and characteristics of the fluid solutions processed by the dialysate system 120, the dialysis machine 100 can include various sensors, particularly electrical sensors, disposed in fluid communication with the system. The sensors may be electrically or electronically actuated and may work on electromagnetic principals to analyze and measure information regarding the fluids that are important to the dialysis process. Measured parameters may include conductivity, temperature, flow rate, pH level, and other characteristics. For example, to analyze and determine the composition and quality of the recycled dialysate before directing it to the dialyzer 110, the dialysis machine 100 can include a supply sensor 150 disposed in the dialysate supply line 122 just upstream of the dialyzer. In addition, to receive and determine the quality and composition of the used dialysate returning from the dialyzer 110 after treatment of the patient's blood, a return sensor 150 can be disposed in the dialysate return line 126 downstream of the dialyzer. The supply and return sensors 150, 152 can also be in electrical communication with the controller 140 to send and receive information between the components. Communication can be established by sending and receiving non-transitory analog or digital signals over communication busses such as conductive wires, optical waveguides, and the like disposed through the dialysis machine 100. Additional electrical sensors can be incorporated at other locations within the dialysate system 120 to monitor other fluid properties.

Conductivity Sensor

To analyze the dialysate of the dialysis machine or other process fluids of similar medical devices, the electrical sensors can be placed in direct fluidic contact with the subject fluid and may include electrical or electronic components disposed to assess electrical or magnetic properties of the fluids. For example, in an embodiment, the electrical sensor can be a conductivity sensor that measures electrical conductivity of the subject fluid. Most liquids have the ability to conduct or pass an electrical current to a degree. The electrical charge is carried by electrolytes or ions, including cations (positive) and anions (negative), present in the fluid. The number of ions in the fluid, and thus the ability of the fluid to conduct or resist electric current, is dependent upon a number of factors including the composition of the fluid, temperature, flow rate, and volume. If factors such as volume and temperature are known and accounted for, then the measurable conductivity of the fluid can be used to deduce the unknown composition of the fluid.

To measure the conductivity of a fluid, the electrical sensor is configured to apply a current or voltage to a volume of the fluid between two predetermined points or locations. The resistivity of the fluid to passing electricity, which is the mathematic reciprocal of conductivity, causes a drop or decrease in the voltage and/or current between the two points. An appropriate electrical meter can measure the decrease in those parameters which are reflective of the fluid's resistivity and thereby establish the conductivity of the fluid by the mathematical relation. The physical and electrical coupling between the electrical sensor and the fluid occurs in a device or unit referred to as a conductivity cell that includes electrodes to apply and sense the voltage and/or current.

Figure 2:
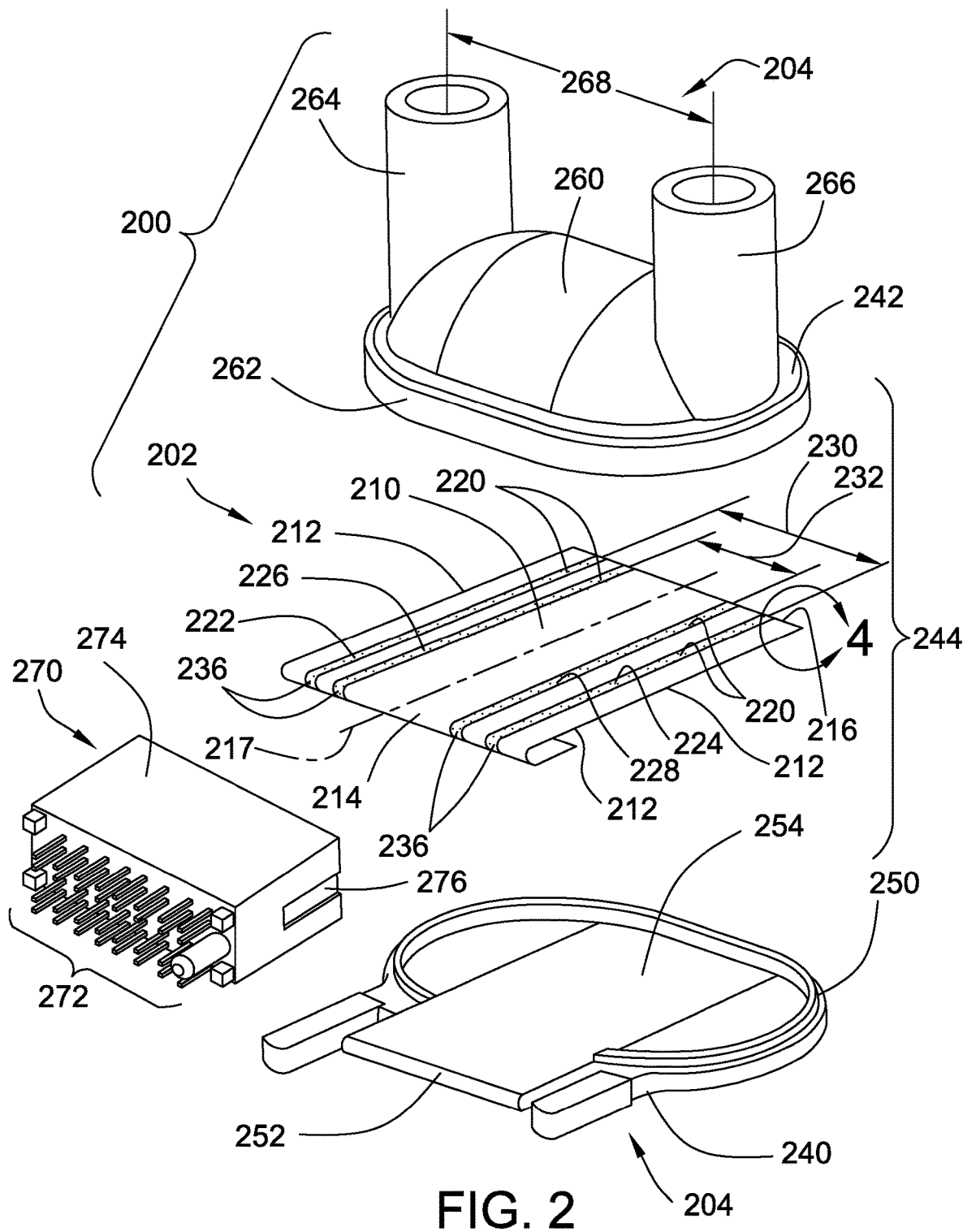
FIG. 2 is an exploded view of one embodiment of the electrical sensor for the dialysis system which utilizes a four-conductor electronic fabric probe disposed in a housing having a flow-over configuration.
Figure 3:
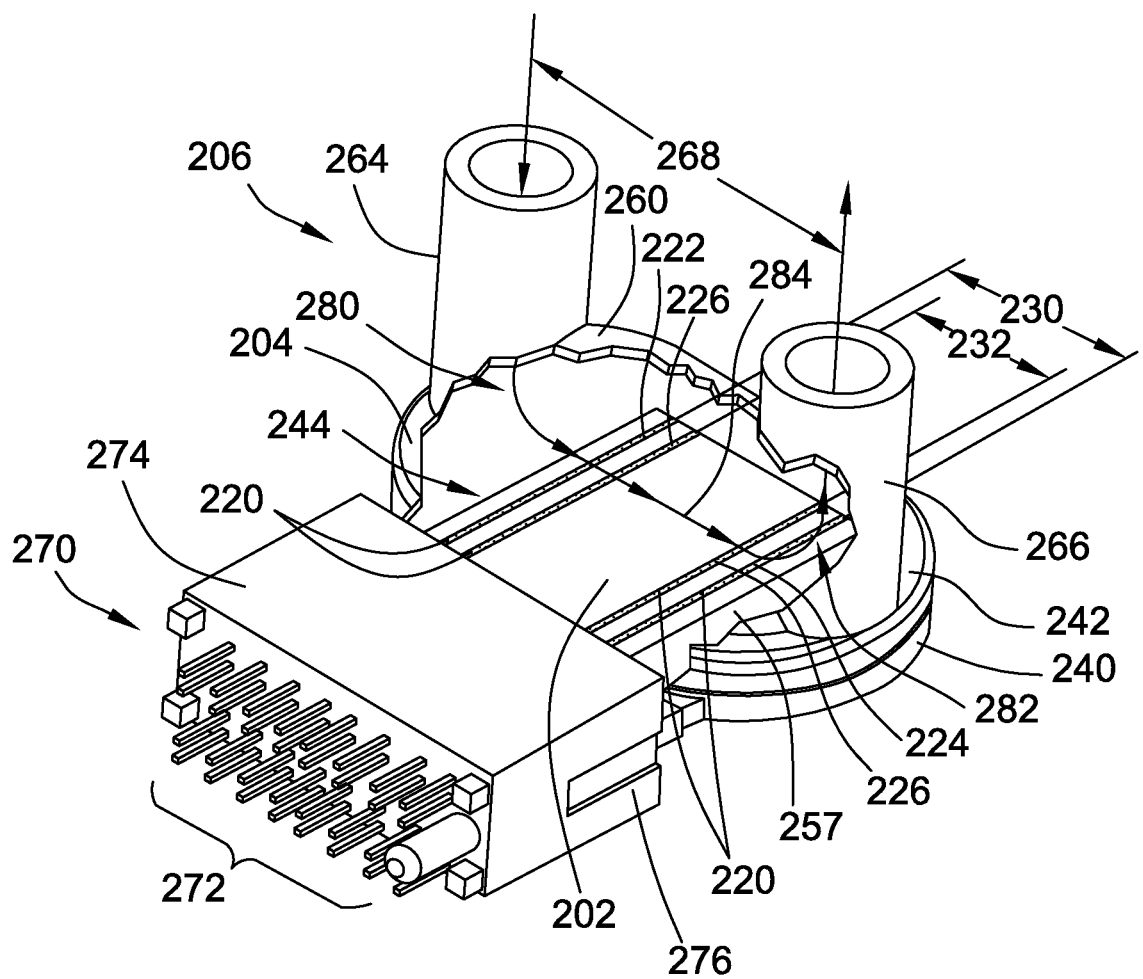
FIG. 3 is a partially cutaway, perspective assembly view of the embodiment of FIG. 2 illustrating the fluid flow through the electrical sensor across the electronic fabric probe.

Referring to FIGS. 2 and 3, there is illustrated an embodiment of an electrical sensor 200 configured to establish fluid communication with the process fluid of a dialysis machine or similar medical device and that includes electrical components such as conductive elements disposed in physical contact with the fluid and thereby function as a conductivity cell. In particular, the electrical sensor 200 includes a probe 202 made from a piece of electronic fabric material having one or more conductive electrodes embedded therein that can be accommodated in a non-conductive housing or enclosure 204 to establish a fluid path across the electronic fabric probe 202. Electronic fabrics or electronic textiles are a class of materials in which electronic components are disposed in fabric-like materials or sheet-like materials, non-conductive in character, and are intended for similar applications as traditional fabrics and textiles. Examples include wearable electronics. A characteristic of electronic fabrics is their flexible, sheet-like structure enables them to cover and conform to a surface. In accordance with an aspect of the disclosure, the electronic fabric probe 202 can be cut or trimmed from a larger swath of electronic fabric material for its specific application in the electrical sensor, thereby facilitating manufacturability of the probes. For example, various sizes and shapes can be cut from the same swath of electronic fabric.

Figure 4:
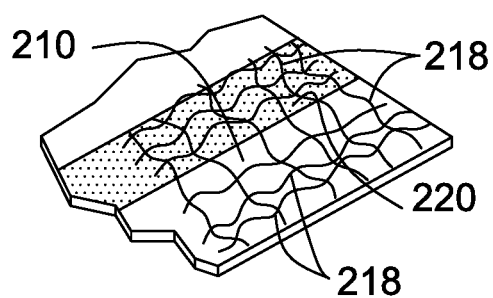
FIG. 4 is a detailed perspective view of the area indicated in FIG. 2 illustrating structural details of an embodiment of the electronic fabric probe.

In the embodiment illustrated in FIGS. 2 and 4, the electronic fabric probe 202 includes a non-conductive fabric layer 210 that may have a planar, polygonal shape delineating a rectangular outline or peripheral edge 212. The polygonal shape further provides a first side edge 214 and a parallel, spaced apart second side edge 216 that extend perpendicular to a centerline 217 of the fabric layer 210. The fabric layer 210 also has a pliable, sheet-like characteristic or property and may be composed of individual fibers 218 or threads of natural or synthetic materials that have been assembled together in an interlocking manner such as by, for example, weaving, knitting, sewing, carding, bonding, matting, pressing, etc. Alternatively, the non-conductive fabric layer 210 can be made from flexible, thinly formed, plastic films. In an embodiment, the non-conductive material for the fabric layer can be made from polyethylene Terephtharlate (PET) mesh. The fabric layer 210 can have some fluid permeability or porosity to facilitate its interaction with the process fluids of the medical device. The thickness of the sheet-like fabric layer 210 and its permeability can be selected based on the application and fluid flow to be encountered.

To provide electrodes for the electronic fabric probe 202, one or more conductors 220, and up to any suitable number of conductors, can be disposed on the fabric layer 210. In the illustrated embodiment, the conductors 220 can be made of thin strips of conductive material woven, stitched, or otherwise embedded into the non-conductive fabric layer 210 in such a manner that at least a portion of the conductor is exposed along a surface of the fabric layer. More specifically, the conductors 220 can be long, thin rectangular threads arranged on the fabric layer to facilitate their electromagnetic utility. Suitable materials for the conductors 220 include stainless steel, aluminum, gold, copper, etc., and the conductors 220 can be stamped from thin metallic sheets or foil, although in other embodiments the conductors can be formed as thin-gauged wires. As illustrated in FIG. 4, in an embodiment, the conductor may be secured to the fabric layer 210 by random fibers extending across the width of the conductors.

Various types of conductivity sensors are available and may include any suitable number of conductors for making selected measurements. For example, in the embodiment illustrated in FIG. 2, the electronic fabric probe 202 can be configured as a four-electrode device and can include a first conductor 222, a second conductor 224, a third conductor 226, and a fourth conductor 228. The first, second, third, and four conductors 222, 224, 226, 228, extend lengthwise between the first side edge 214 and the second side edge 216 of the non-conductive fabric layer and are arranged parallel to and spaced apart from each other with respect to the centerline 217. Further, the first and second conductors 222, 224 can be directed outwardly toward the peripheral edges 212 by a given first distance 230 with respect to the centerline 217 while the third and fourth conductors 226, 228 are directed inwardly of the first and second conductors and spaced apart a second distance 232 that is less than the first distance. The first and second distances 230, 232 are generally maintainable because the conductors 220 are embedded in the fabric layer 210 by stitching, weaving, etc. The terminal ends of the four conductors along the first side edge 214 can form a respective plurality of leads or terminals 236 for the electronic fabric probe 202.

To accommodate the electronic fabric probe 202, the enclosure 204 illustrated in FIG. 2 can be configured as a two-piece construction having a first enclosure portion 240 and a second enclosure portion 242 that, when assembled together, can delineate an enclosed fluid chamber 244. The first enclosure portion 240 can be a lower portion formed as a flat, planar structure having an oblong or oval shape delineating an oval-shaped outline 250. Projecting from one side of the oval-shaped outline 150 can be a connector tongue 252, the utility of which is described more fully below. Disposed into a surface of the flat first enclosure portion 240 can be a slight depression 254 extending along the connector tongue 252 toward the opposite edge of the oval-shaped outline 150. The width of the depression 254 can correspond generally to the width of the fabric layer 210 measured perpendicularly to the centerline 217. Accordingly, in the present embodiment, the electronic fabric probe 202 can be placed in the depression 254 adjacent the planar surface of the first enclosure portion 240 when the first enclosure portion is assembled to the second enclosure portion 242. When so assembled, the first side edge 214 of the fabric layer 210 can align along the connector tongue 252 where the terminals 236 of the conductors 220 can be exposed externally of the enclosure 204.

To create the fluid chamber 244, the second enclosure portion 242 can be formed as a hollow dome 260 extending upwardly from an oval-shaped base 262 that corresponds to the oval-shaped outline 250 of the lower enclosure portion 240. The dome 260 can delineate a hollow cavity underneath that corresponds generally to the fluid chamber 244. The cross-sectional area and/or the volume of the fluid chamber 244 can be predetermined by the shape of the dome 260, which may be advantageous for reasons explained below. To connect the electrical sensor 200 to the tubes or hosing of the dialysate system, the second enclosure portion 242 includes an upwardly extending fluid inlet 264 and a corresponding fluid outlet 266 that may be configured as cylindrical hose fittings. Connection may be established by press-fitting, hose clamps, etc. The fluid inlet 264 and the fluid outlet 266 are parallel to and spaced apart from each other toward opposite ends of the oval-shaped base 262 by a third distance 268 that may be larger than either the first or second distances 230, 232 associated with the fabric layer 210. The first enclosure portion 240 and the second enclosure portion 242 can be made of any suitable non-conductive material including, for example, molded polycarbonate. The first and second enclosure portions 240, 242 can be joined together, in a snap-fit relation, by clamps, etc. such that the enclosure 404 can be readily assembled and disassembled.

To establish electronic communication with the conductors 220 on the electronic fabric probe 202 when accommodated in the assembled enclosure 204, the electrical sensor 200 can be operatively associated with an attachable electrical connector 270. The electrical connector 270 can be in the form of a pin header having a plurality of conductive leads or pins 272 arranged in and projecting from an insulative box or shroud 274. The electrical connector can further include a slot 276 disposed in the shroud 274, opposite the side from where the pins 272 project, that enables the connector to receive and attach to the connector tongue 252 extending from the lower enclosure housing 240.

Accordingly, a portion of the pins 272 can make electrical contact with the terminals 236 of the conductors 220 along the first side edge 214 of the fabric layer 210. When the electrical sensor 200 is disposed in the dialysis machine or similar medical device, the electrical connector 270 can mate with a corresponding receptacle in the device to establish electrical communication between the electrical sensor 200 and a controller of the dialysis machine or similar device.

The flow of process fluids through the electrical sensor 200 and the conductivity measurements obtained can be described with respect to FIG. 3. In particular, separate areas of the fluid chamber 244 can be further designated as an entry region 280 corresponding to the fluid inlet 264 and disposed toward one end of the oblong-shaped enclosure 204 and an exit region 282 corresponding to the fluid outlet 266 and disposed toward the opposite end of the enclosure. The electronic fabric probe 202 adjacent the lower first enclosure portion 240 is exposed to the fluid chamber 244 with its upper surface directed toward the fluid inlet 264 and fluid outlet 266. Fluid flowing inwardly into the entry region 280 and perpendicular to the lower enclosure portion 240 will accordingly be redirected horizontally along a fluid flow path 284 to the exit region 282 at the opposite end of the oblong enclosure 204. Further, the flow path 284 is generally perpendicular to and leads across each of the conductors 220 embedded in the electronic fabric probe 202 with each of the conductors traversing the flow path. Preferably, because the electronic fabric probe 202 is disposed in the depression 254 formed in the lower first enclosure portion 240, the position of the probe will be maintained as fluid is directed between the fluid inlet 264 and the fluid outlet 266. Further, because the conductors 220 are stitched or woven into the fabric layer, their relative positions with respect to each other are generally fixed at the predetermined first distance 230 and the predetermined second distance 232. The exposure of the conductors on the fabric layer and the fluid permeability associated with the fabric layer facilities electrical connection between the conductors and the process fluids.

In a four-electrode conductivity cell, two outer electrodes, corresponding here to the first conductor 222 and the second conductor 224, can be designated excitation electrodes. The excitation electrodes are coupled to a power source to apply a voltage or current between the first and second conductors 222, 224 causing a current to be conducted through the fluid in the internal chamber 244. The power source may supply either alternating current (AC) or direct current (DC) electricity. Because the process fluids are typically imperfect conductors, the fluid will cause a voltage drop between the first and second conductors 222, 224. The value of the voltage drop corresponds to the composition of the fluid, such as the presence or absence of ions, impurities, etc. To measure the voltage drop, the inner two electrodes, corresponding to the third and fourth conductors 226, 228, can be designated sense electrodes, or ground guards. The sense electrodes can be coupled to an appropriate meter such as an amp meter, an ohm meter, or preferably a voltage meter that senses the voltage drop between at least the third and fourth conductors 226, 228. The meter in turn can be coupled to or part of a controller such as described above to perform the following calculations. The measured voltage drop can be converted to the electrical resistance provided by the fluid between the sense electrodes according to Ohm's law:

Ohm's Law: $V=I/R$ (Eqn. 1)

Wherein V is the voltage drop, in volts;
I is the current, in amps or milliamps; and
R is the resistance, in ohms or milliohms.

Because the second distance 232 between the third and fourth conductors 226, 228, i.e., the sense electrodes, is predetermined by the arrangement of the electronic fabric probe 202, the calculated electrical resistance in ohms between the third and fourth conductors can be converted to the resistivity of the fluid. Resistivity is an intrinsic property of the fluid that quantifies how strongly it will oppose the flow of current and is typically presented in units of ohm*centimeters ($\Omega$*cm). Resistivity can be approximated by calculating the product of the measured and calculated resistance in ohms and the predetermined cross-sectional area A of the interior chamber 244 in $cm^2$, and dividing that value by L, the second distance 232 in cm:

$\rho = R*A/L$ (Eqn. 2)

Because conductivity is the mathematical inverse of resistivity, the conductivity of the fluid flowing in the electrical sensor 200 is readily determined. Once the conductivity for the process fluid is calculated, it can be compared to empirically predetermined values to determine the composition or content of the process fluid, which provides discernible information about the dialysis process and indications on how it may be adjusted. The relationship between the above formulas and the characteristics of the process fluids may not be precisely linear or directly proportional, however, and may require calibration or estimation of calculated and determined values.

According to one advantageous embodiment, all or part of the electrical sensor 200 can be disposable. In particular, because the enclosure 204 connects to the fluid circuitry of the dialysis machine via hoses, the electrical sensor 200 can be readily removed from the dialysis machine during a cleansing process after use. Further, because the enclosure 204 can be readily disassembled into the separate first and second enclosure portions 240, 242, the electronic fabric probe 202 can be removed and discarded after use. The first and second enclosure portions 240, 242 can be sterilized and reused with a new electronic fabric probe 202 installed, or the entire electrical sensor can be discarded. Because the electrical sensor 200 necessarily contacts dialysate and other process fluids, the disposable aspect of all or part of the sensor improves its utility in medical and biological applications such as dialysis treatments.

Figure 5:
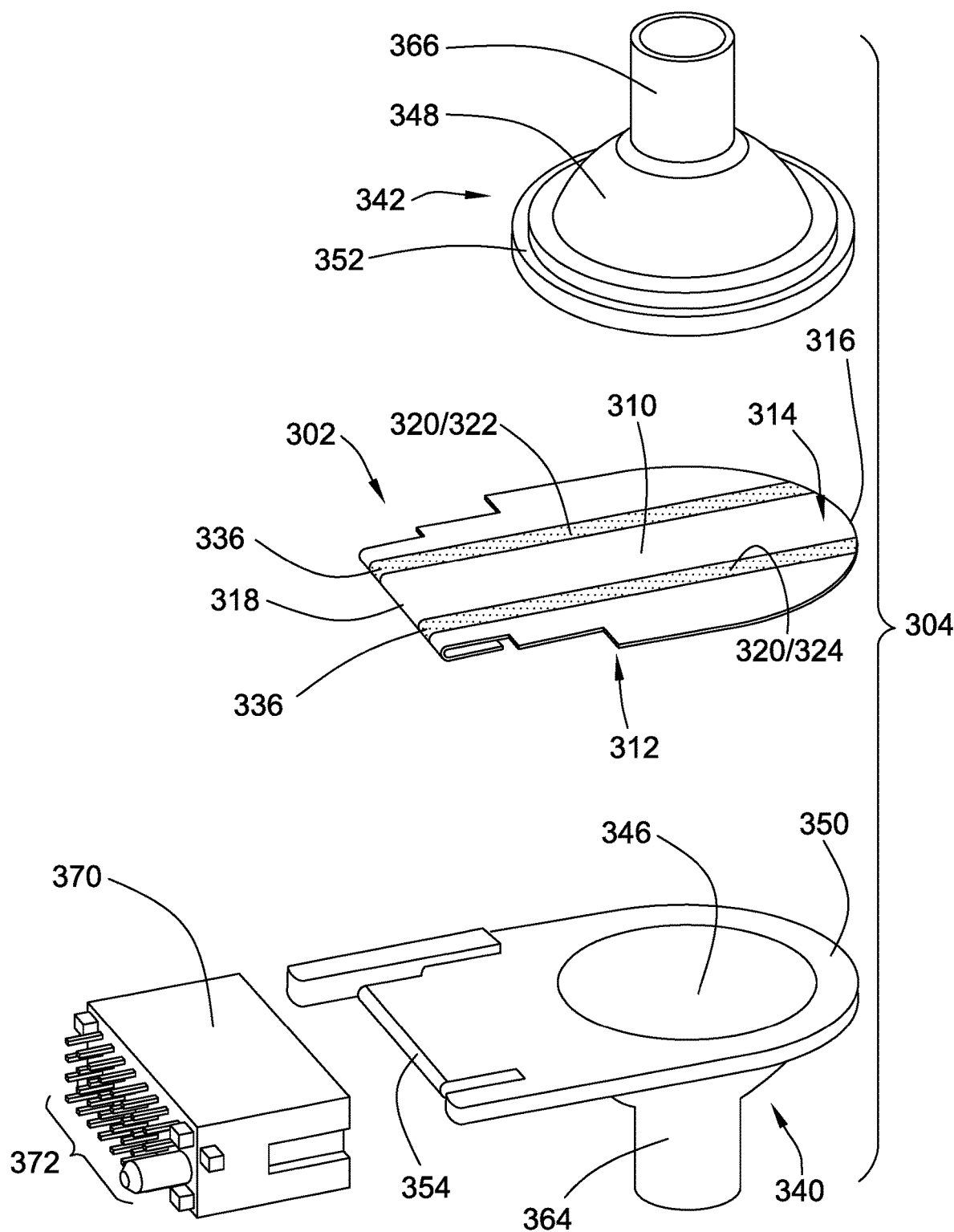
FIG. 5 is an exploded view of another embodiment of the electrical sensor that utilizes a two-conductor electronic fabric probe disposed in a housing having a flow-through configuration.
Figure 6:
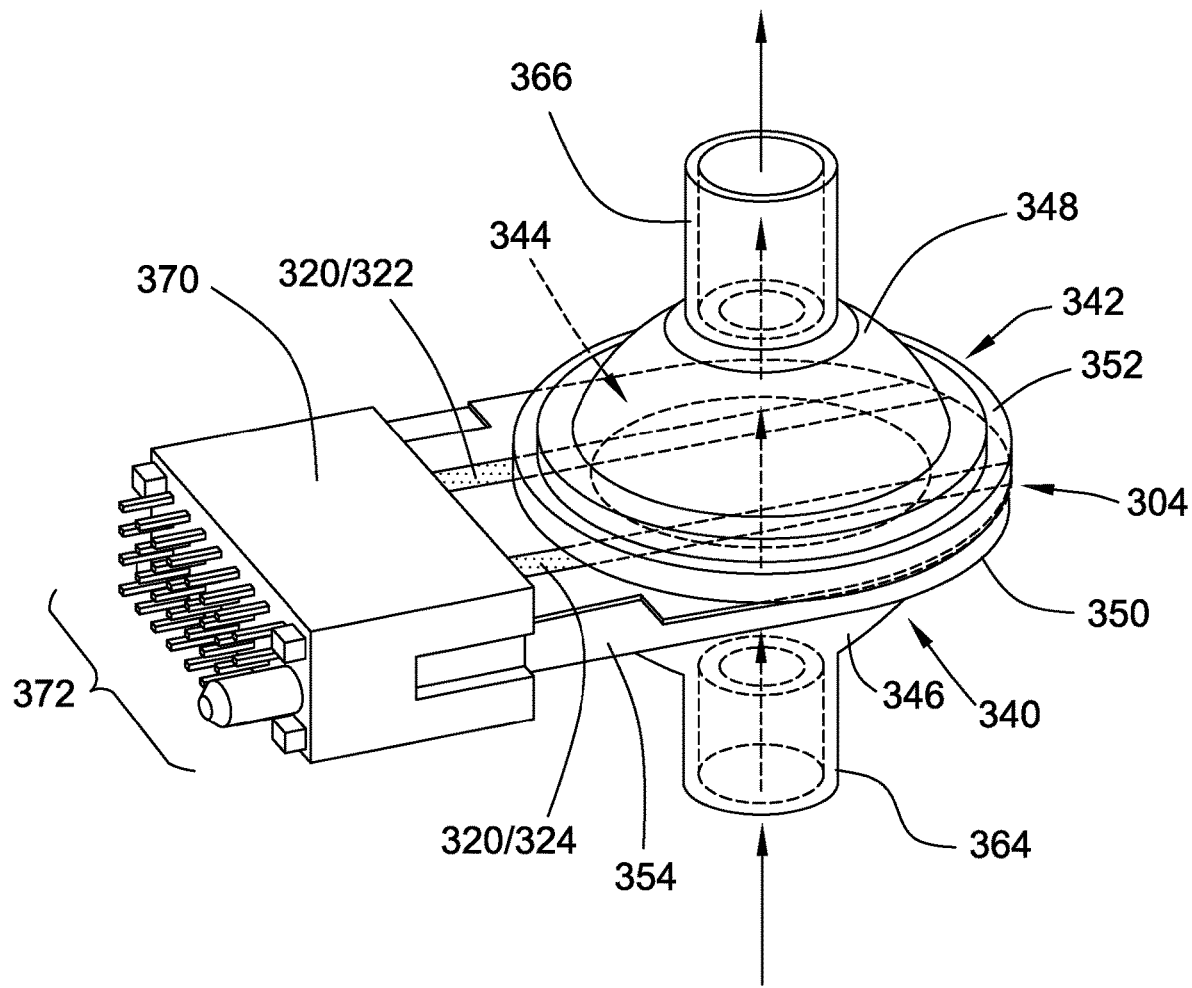
FIG. 6 is a perspective assembly view of the embodiment of FIG. 5 illustrating fluid flow through the electrical sensor, with the enclosed elements represented in dashed lines.

While the embodiment of the electronic fabric probe illustrated in FIGS. 2 and 4 has a four-electrode configuration, other configurations for the probe are possible including, for example, a two-electrode embodiment and a three-electrode embodiment. In addition, configurations other than the flow-over configuration are possible. Referring to FIGS. 5 and 6, there is illustrated a two-electrode, flow-through configuration for the electrical sensor 300 to analyze fluids in a dialysis machine or similar medical device. The electrical sensor 300 includes an electronic fabric probe 302 that can be accommodated in a two piece, non-conductive enclosure 304 configured to direct process fluids through the fabric probe. The electronic fabric probe 302 can be similar in construction to the probe described above and can include a flexible, planar fabric layer 310 with a plurality of conductors 320 disposed in it. To enable fluid to permeate through the fabric layer 302 from a first surface 312 to a second surface 314, the fabric layer 310 may be relatively porous or made from loosely woven, knitted, or matted fibers. Moreover, in the present embodiment, the fabric layer 310 can have a tongue-shaped outline including a curved peripheral edge 316 and a square or rectangular extension 318.

To function as the electrodes, the electronic fabric probe 302 can include a plurality of conductors 320 including a first conductor 322 and a second conductor 324 embedded in the fabric layer 310. The first conductor 322 and the second conductor 324 can be relatively thin, elongated strips of conductive material and can extend, parallel and spaced apart, lengthwise across the fabric layer 310 from the curved peripheral edge 316 to the rectangular extension 318. The first and second conductors 322, 324 can form terminals 336 where they terminate at the edge of the rectangular extension 318.

To accommodate the electronic fabric sensor 302 in a flow-through configuration, the enclosure 304 has a two-piece construction including a first or lower enclosure portion 340 and a second or upper enclosure portion 342 that can be assembled together to delineate an fluid chamber 344. In the illustrated embodiment, the lower enclosure portion 340 and the upper enclosure portion 342 can each have a respective hemispherical shaped dome 346, 348 that delineates a correspondingly hemispherical shaped cavity. It should be noted, however, that terms like "lower," "upper," "down," and "up" are for reference only and should not be construed as a limitation on the claims unless explicitly stated. The hemispherical domes 346, 348 can be of the same general dimensions. When assembled together, the first and second hemispherical domes 346, 348 provide the chamber 344 with a spherical shape. The lower and upper hemispherical domes 346, 348 can also include respective circular bases 350, 352 of corresponding diameters that mate together as flanges when the lower and upper enclosure portions 342, 344 are assembled. Extending perpendicularly from the circular base 350 of the lower enclosure portion 340 can be a flat, planar connector extension 354 corresponding to the rectangular extension 318 of the electronic fabric conductor 302.

When the electrical connector 300 is assembled, the electronic fabric conductor 302 is suspended in the spherical chamber 344 with the first surface 312 directed toward the lower hemispherical dome 346 and the second surface 314 directed upwardly toward the upper hemispherical dome 348. The curved peripheral edge 316 of the electronic fabric conductor 302 can be sandwiched between the first and second circular bases 350, 352. To direct fluid across the spherical chamber 344 and through the electronic fabric conductor 302, the lower enclosure portion 340 can include a downwardly directed fluid inlet 364 and the upper portion 342 can include an oppositely directed, upward fluid outlet 364. The oppositely disposed fluid inlet 364 and fluid outlet 366 delineate a fluid flow path 368 similar to an axis line disposed across the spherical fluid chamber 344. Process fluid introduced to the electrical sensor 300 through the fluid inlet 364 must permeate and traverse across the electronic fabric sensor 302 to reach the fluid outlet 366. If a power source is applied to the first conductor 322 designating it an excitation electrode, current will be conducted through the fluid across the electronic fabric probe 302 to the second conductor 324 that functions as a sense electrode. To establish electrical communication with the first and second conductors 322, 324 to apply and sense voltage and/or current, an electrical connector 370 including a plurality of conductive pins 372 can be attached to the connector extension 354 of the lower enclosure portion 340.

Flowrate Sensor

Figure 7:
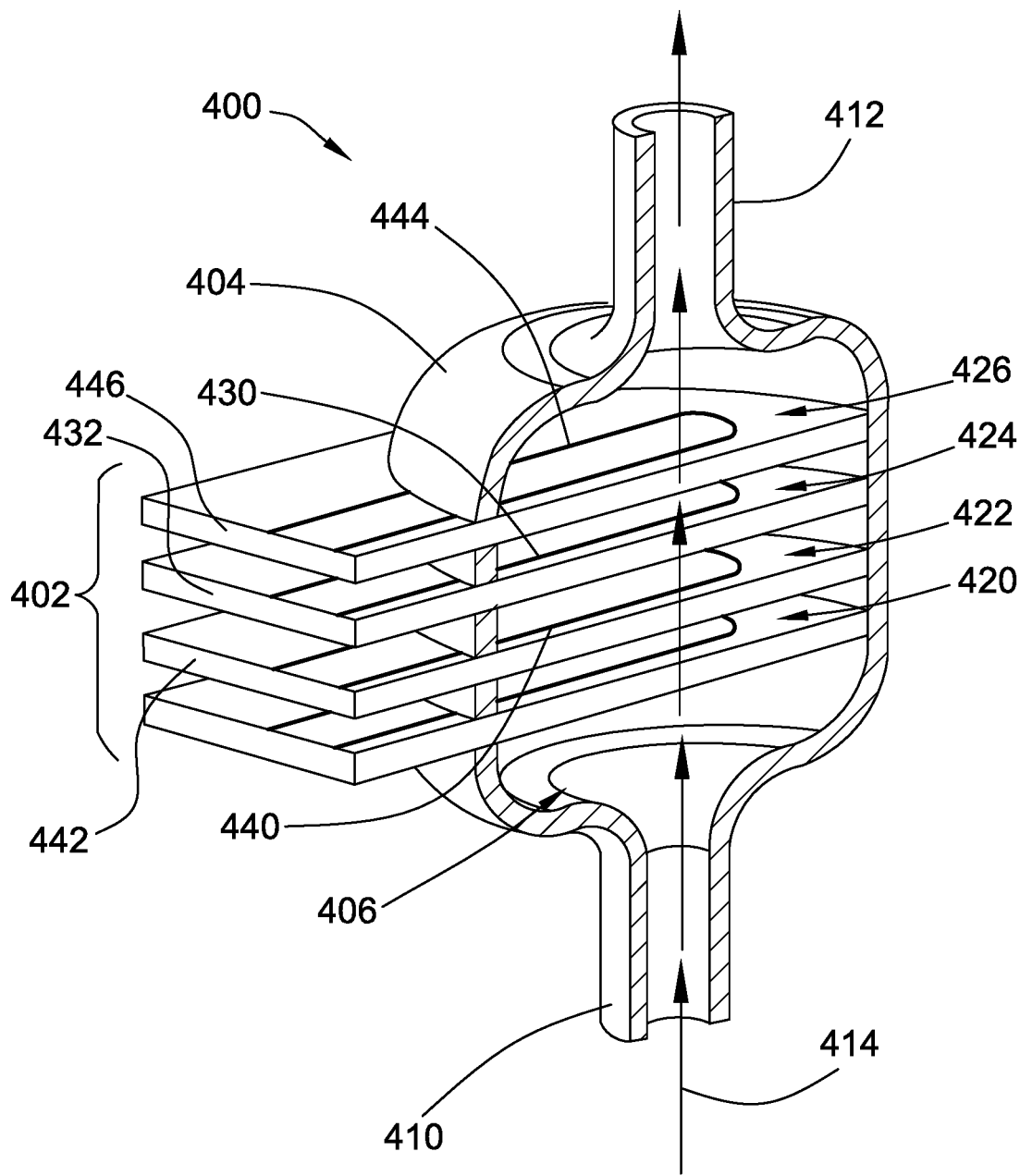
FIG. 7 is a partially cutaway perspective view of another embodiment of the electrical sensor that utilizes a plurality of electronic fabric probes for analyzing different aspects of the fluid utilized in the dialysis process.

In addition to measuring conductivity of a process fluid, electrical sensors of the foregoing type can be configured to measure other parameters and characteristics of the fluids processed through a medical device such as a dialysis machine. Referring to FIG. 7, there is illustrated an embodiment of an electrical sensor 400 having a plurality of electronic fabric probes 402 arranged to measure flow rate through the sensor in addition to conductivity. The plurality electronic fabric probes 402 are accommodated in a non-conductive enclosure 404 that defines an internal fluid chamber 406 in which the probes are suspended. The enclosure 404 is generally drum shaped so the fluid chamber 406 delineates a heightened cylinder in which the electronic fabric probes 402 are vertically disposed. To establish a flow-through configuration for the electrical sensor 400, the enclosure 404 can have a downward fluid inlet 410 and an oppositely directed upward fluid outlet 412 that delineate a flow path 414 through the probes 402 and across the fluid chamber 406. Portions of the electronic fabric probes 402 protrude radially outward from a side of the enclosure 404 for connecting with associated equipment.

The first electronic fabric probe 420, disposed lowest in the fluid chamber 406, can measure the conductivity of the process fluid and can have any of the foregoing configurations. The second, third, and fourth electronic fabric probes 422, 424, and 426 can be arranged to determine flow rate through the fluid chamber 406 by sensing temperature differences in the fluid. In particular, the third electronic fabric probe 424 may be a heating probe and may include one or more heating conductors 430, in the structural form of metallic wires or threads, embedded in the non-conductive fabric layer 432 of the third electronic fabric probe. The heating conductors 430 may have a sufficient electrical resistance causing them to heat when a current is applied to the third electronic fabric probe 424. The heating conductors 430 can transfer the generated heat to the fluid flowing through the third electronic fabric probe 424. The second and fourth electronic fabric probes 422, 426, arranged above and below the third electronic fabric probe 424, can be configured as thermal sensing probes. For example, the second electronic fabric probe 422 can include a first sensing conductor 440 embedded in the respective fabric layer 442 that is formed as a closed loop or circuit leading into and out of the fluid chamber 406. The electrical resistance associated with the first sensing conductor 440 can be proportionally dependent upon temperature and changes according to an increase and decrease in the temperature of the surrounding environment. The fourth electronic fabric probe 426 can include a similarly arranged second sensing conductor 444 embedded in the respect fourth fabric layer 446.

In operation, as the process fluid from the fluid inlet 410 flows along the flow path 414 and permeates through the second electronic fabric conductor 422, a meter operatively associated with the first sensing conductor 440 can determine its resistance by measuring the voltage drop over the first sensing conductor. The process fluid next permeates the third electronic fabric probe 424 where the heating conductor 430 can transfer generated heat to the fluid flowing past it. The second sensing conductor 444 disposed in the fourth electronic fabric probe 426 can also be operatively associated with a meter that determines the resistance of the second sensing conductor by measuring the associated voltage drop. The resistance measurements between the first sensing conductor 440 and the second sensing conductor 444 can be compared to determine the temperature difference between the second electronic fabric probes 422 and the fourth electronic fabric probes 426. If the heat energy input through the heating conductor 430 is known, the flow rate of process fluid through the fluid chamber 406 is readily solvable. In further embodiments, the electrical sensor can measure other qualities and parameters such as temperature.

Figure 8:
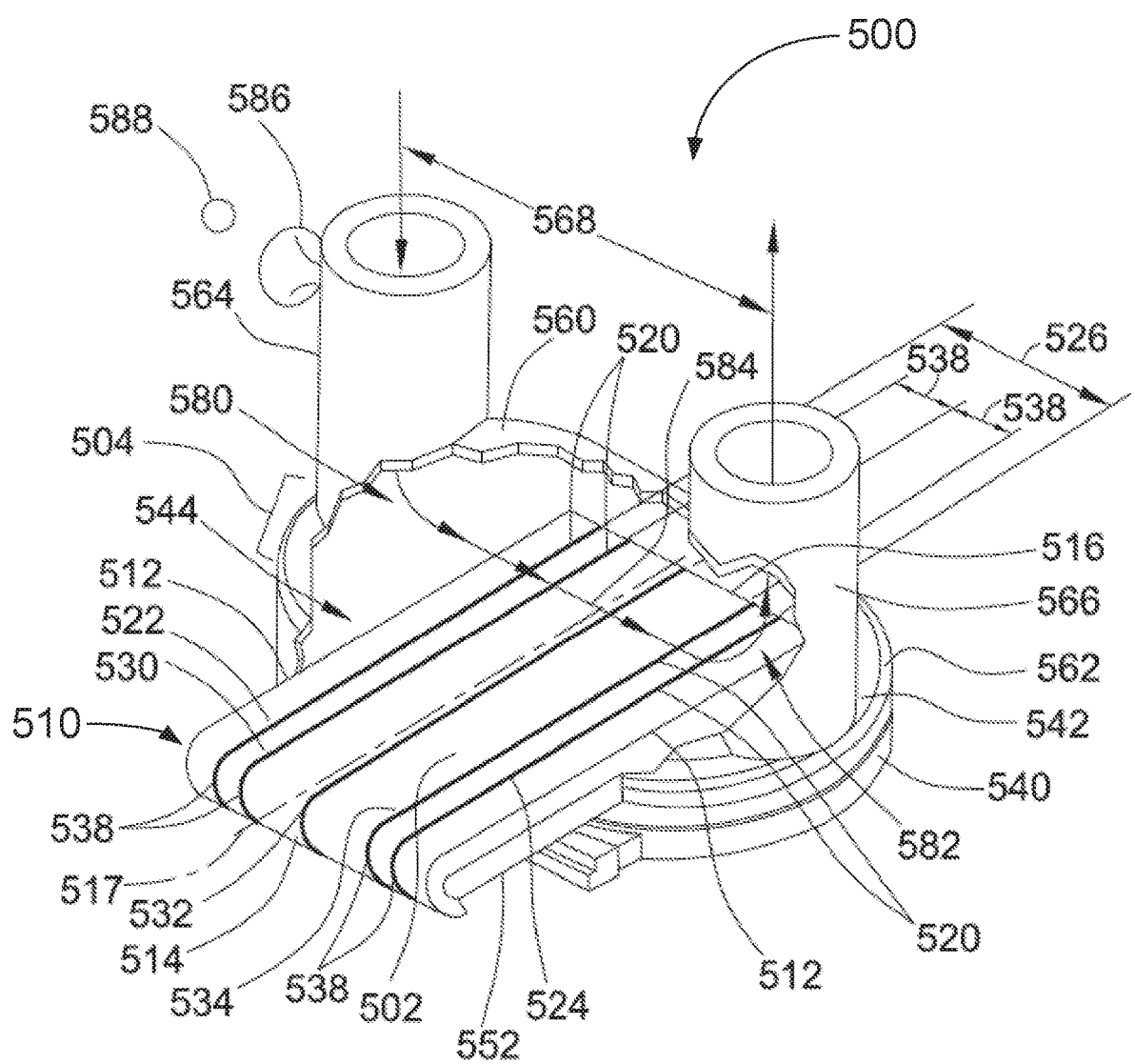
FIG. 8 is a partially cutaway perspective view of another embodiment of the electrical sensor having at least five electrical conductors embedded in the electronic fabric probe to measure the flow rate of fluid through the electrical sensor.

Referring to FIG. 8, there is illustrated another embodiment of an electrical sensor 500 configured for measuring conductivity and flow rate of a process fluid in a medical device or the like using an electronic fabric probe 502 partially contained in a probe enclosure 504. The electronic fabric probe 502 and the probe enclosure 504 can be similar in shape and configuration to the fabric probe 202 and the enclosure 204 described with respect to FIGS. 2 and 3, and the components may complementarily engage or support each other in a similar manner as well. Accordingly, the electronic fabric probe 502 can include a non-conductive fabric layer 510 that is thin and planar in shape and is made from natural or synthetic fabric or cloth of interlocking fibers or, in other embodiments, is made from plastic films. The non-conductive fabric layer 510 has a pliable and flexible characteristic and can adapt or conform to different shapes or be folded upon itself. The fabric layer 510 may be rectangular including elongated side edges 512 that extend between a shorter front edge 514 and a rear edge 516. For reference purposes, disposed between the side edges 512 and perpendicular to the front and rear edges 514, 516 is the centerline 517 of the rectangular non-conductive fabric layer 510.

To function as the electrodes for conducting electricity, the electronic fabric probe 500 can include one or more electrode conductors 520 disposed on the fabric layers 502. As before, the electrode conductors 520 can be elongated, thin strips or tapes of conductive material embedded in the non-conductive fabric layer 510 by stitching, weaving, or otherwise so that the conductors are partially exposed along the surface of the electronic fabric probe 500 for making electrical contact with other elements. However, in other embodiments, the electrode conductors 520 can be made from wires or may be formed by depositing, spraying or adhering powdered or liquid conductive materials to the non-conductive fabric layer. The electrode conductors 520 can be made from any suitable conductive material including stainless steel, aluminum, gold, copper, and are preferably thin enough to avoid adding significant rigidity to the flexible non-conductive fabric layer 510.

In the illustrated embodiment where the electrical sensor 500 measures conductivity and flow rate, the plurality of electrode conductors 520 can have at least five (5) conductors including a first conductor 522 and a second conductor 524 disposed towards either of the longer side edges 500 on opposing sides of the fabric centerline 517. The first and second conductors 522, 524 may be spaced-apart from each other by a first distance 526 indicated by the arrow. The plurality of electrode conductors 520 can also include a third conductor 530, a fourth conductor 532, and a fifth conductor 534 disposed between the first and second conductors 522, 524. The five electrode conductors 520 extend across the non-conductive fabric layer 510 in a parallel alignment to each other and to the side edges 512 from the front edge 514, where the tips of the conductors 520 may form leads or terminals 536, to the rear edge 516. The five electrode conductors 520 may be distinct and separated from each other to maintain electrical isolation. In this regard, the third conductor 526, fourth conductor 527, and fifth conductor 528 can be evenly spaced from each other a second distance 538, with the fourth conductor 532 disposed generally along the centerline 517 and the third and fourth conductors 530, 534 offset toward the side edges 512 and the respective first and second conductors 522, 524.

In the illustrated embodiment, the first and second conductors 522, 524 can be designated as first and second excitation electrodes while the third, fourth and fifth conductors 530, 532, 534 may be designated as first, second, and third sense electrodes respectively. When the electronic sensor 500 is mated with an electrical connector and connected to the electrical system of a medical device or the like, such as the controller 140 operatively associated with the dialysis machine 100 of FIG. 1, the first and second excitation electrodes 522, 524 can be in electrical communication with a power source supplying voltage and/or current. The supplied power may be alternating current (AC) or direct current (DC) and the current may flow or be conducted between the first and second excitation electrodes 522, 524 when the electronic fabric probe 502 is suspended in a fluid. To measure the voltage drop between the first and second excitation electrodes 522, 524, the first, second, and third sense electrodes 530, 532, 534 can be electrically connected to an appropriate meter. As described above, the voltage drop measured between the sense electrodes 530, 532, 534 can be converted by Ohm's law to the electrical resistance of the fluid, which can be inverted to determine the fluid conductivity. Hence, the electrical sensor 500 measures conductivity similar to the embodiment of FIGS. 2 and 3.

To support and position the electronic fabric probe 502 with respect to the fluid to be measured, the probe enclosure 504 can be a two-piece construction having a first enclosure portion 540 and a second enclosure portion 542 that define an enclosed fluid chamber 544 when assembled together. The first enclosure portion 540 is the lower portion having a flat, oval-shape with an outward protruding connector tongue 552 over which the electronic fabric probe 502 lies. To provide the fluid chamber 544, the second enclosure portion 542 is the upper portion having a hollow, dome-like configuration including an upward extending dome 560 rising from an oval-shaped base 562 that mates with the correspondingly shaped first enclosure portion 540. The first and second enclosure portions 540, 542 can be made from any suitable non-conductive material including polycarbonate.

To direct the fluid into the probe enclosure 504 and in contact with the electronic fabric probe 502, the second enclosure portion 542 can have a fluid inlet 564 and a corresponding fluid outlet 566 extending upwardly from the dome 560. The fluid inlet 564 and the fluid outlet 566 may be cylindrical tubes or hose barbs and are parallel to each other and are located at opposite ends of the oval-shaped base 562 as spaced-apart by a third distance 568. The fluid inlet 564 therefore directs fluid into an entry region 580 of the fluid chamber 544 while the fluid outlet 564 directs fluid from an oppositely located exit region 582. The configuration therefore defines a flow-over arrangement for the flow path 584 with fluid entering the fluid chamber 544 perpendicularly to the lower first enclosure portion 540, being redirected perpendicularly to follow across the electronic fabric probe 502 supported on the first enclosure portion, then being redirected to exit the fluid chamber 544. The third distance 568 between the entry region 580 and the exit region 582 can be larger in dimension than the first and second distances 526, 538 defined between the electrode conductors 520 so the flow path perpendicularly crosses all the conductors. While the illustrated flow path 584 through the flow chamber 544 is U-shaped, in other embodiments the fluid inlet 564 and the fluid outlet 566 may be axially aligned so the flow path 584 is straight through the fluid chamber 544 and across the electronic fabric probe 502. In other embodiments, the flow path 584 may have other configurations or directions.

Because the second distance 538 between the first and second sense electrodes 530, 532 and the second distance 538 between the second and third sense electrodes 534, 536 are equal, the measured voltage drop between those second distances 538 should also be equal, assuming the fluid has a consistent conductivity. To measure the flow of the fluid in the fluid chamber 544, a tracer or bolus can be introduced through a bolus introduction port 586 disposed upstream of the entry region 580, for example, possibly in or upstream of the fluid inlet 564. The tracer bolus 588 can be air bubbles, a fluid, or a flowing material that may have similar viscosity and density characteristics as the process fluid being measured but with different electrical characteristics including a different conductivity. When the tracer bolus 588 is directed along the flow path 584 proximate the first and second sense electrodes 530, 532, the voltage drop and, relatedly the conductivity, measured by those electrodes will change accordingly. A brief time later, when the tracer bolus 588 crosses the second and third sense electrodes 532, 534, the voltage drop and conductivity will similarly change while the voltage drop and conductivity between the first and second sense electrodes can return to that of the process fluid. The temporal difference between the bolus tracer 588 crossing the first, second, and third sense electrodes 530, 532, 534 can be recorded and converted to the flow rate, in mm-per-sec or similar units, of the fluid in the fluid chamber 544. In other words, the three equally spaced sense electrodes 530, 532, 534 can measure the travel time of the bolus tracer 588 across the electronic fabric probe 502 with can correspond to the flow rate of the fluid carrying the bolus tracer. Hence, the present embodiment of the electrical sensor 500 can measure both the fluid conductivity and the fluid flow rate.

In an embodiment, the five-conductor electronic fabric probe 502 may provide a self-diagnostic feature due to the arrangement of the electrode conductors. Specifically, if the second distance 538 between the first sense electrode 530, second sense electrode 532, and third sense electrode 534 is the same, they should theoretically sense the same conductivity or voltage drop between the three sense electrodes if the fluid flowing across them has a consistent conductivity. Hence, if the measured voltage or conductivity between the first and second sense electrodes 530, 532 differs from the measurement made between the second and third sense electrodes 532, 534 by more than an acceptable tolerance, that may indicate a problem with the electrical sensor 500. The bolus induction port 586 can be used to introduce fluid of known conductivities for this diagnostic purpose.

While the present embodiment utilizes a series of three sense electrodes to measure the passing conductivity differences, it can be appreciated that in other embodiments, additional sense electrodes can be used to take multiple measurements at various different locations across the electronic fabric probe. It should also be appreciated the electronic fabric probe can be accommodated in significantly different enclosures providing different flow paths for the fluid of interest.

Fluid Pressure or Proximity Sensors

In another aspect of the disclosure, the electrical sensor including an electronic fabric probe can measure characteristics in addition to fluid conductivity such as fluid pressure or its ability to distort or displace the flexible electronic fabric probe with respect to a reference. More specifically, changing the proximity of the electronic fabric probe with respect to the reference by altering the force or pressure applied to the electronic fabric probe can result in the change of a measureable electrical characteristic. Therefore, the measured characteristic can be related back the change in fluid pressure, which may be indicative of another action or property of the medical device. The variable electrical characteristic can be the capacitance or inductance associated with the electronic fabric probe.

Figure 9:
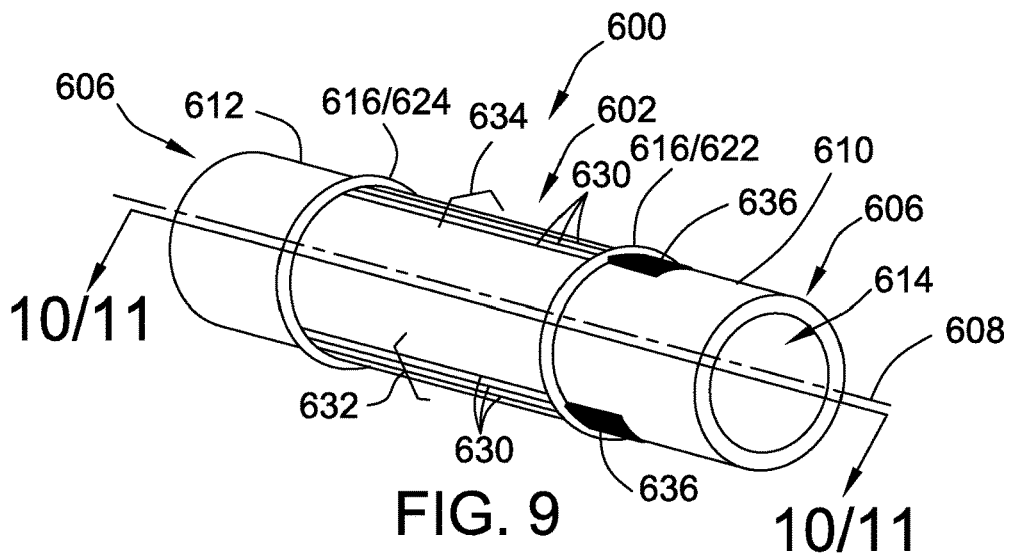
FIG. 9 is a perspective view of another embodiment of the electrical sensor in which the electronic fabric probe is arranged in a tubular, flow-through configuration to measure fluid pressure via the capacitance associated with the probe.
Figure 10:
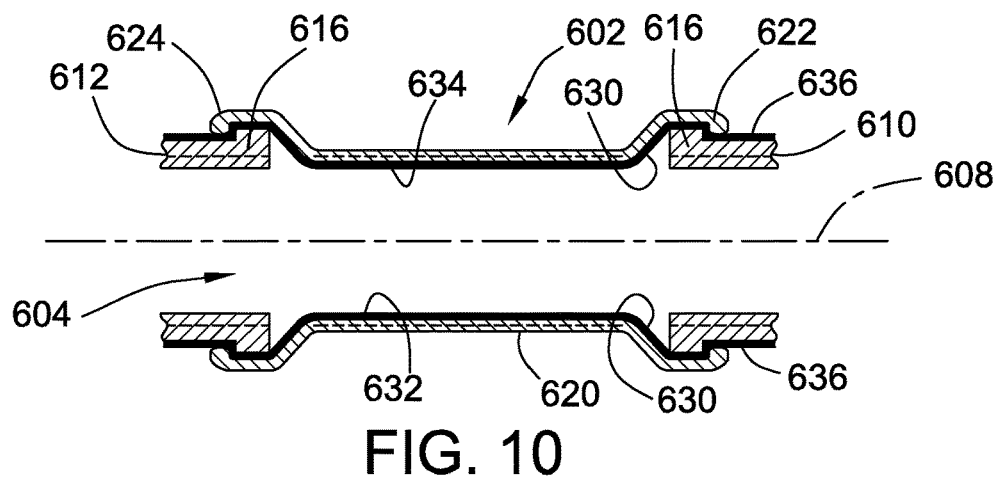
FIG. 10 is a cross-sectional view taken along line 10-10 of FIG. 9 showing the electrical sensor with the electronic fabric probe disposed under a state of normal fluid pressure.
Figure 11:
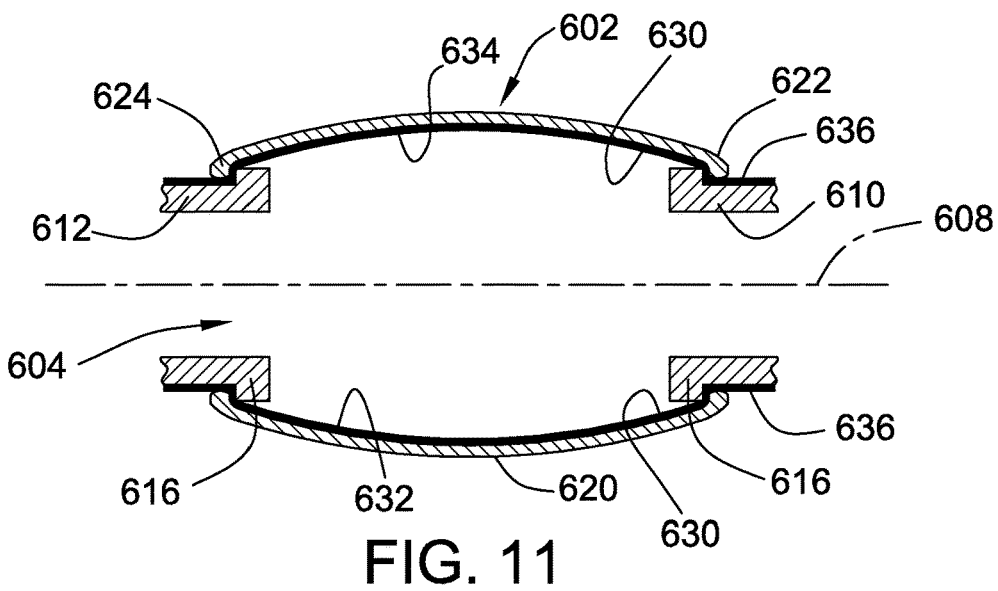
FIG. 11 is a cross-sectional view similar to FIG. 10 showing the electronic fabric probe disposed under a state of increased or excessive fluid pressure.

For example, referring to FIGS. 9, 10, and 11, there is illustrated an embodiment of an electrical sensor 600 configured as an tubular, flow-through element that measures an electrical characteristic of an electronic fabric probe 602 that correspondingly changes dimensions in response to the fluid pressure therein. The electronic fabric probe 602 can be a hollow, tubular structure that defines an internal fluid chamber 604 for receiving the fluid to be analyzed. To support the electronic fabric probe 602 and direct fluid into it, the electrical sensor 600 can include a rigid support body 606 that maintains the tubular shape of the electronic fabric probe 602 thereby defining a longitudinal axis line 608 extending between opposing ends. The support body 606 can include a first end cap 610 and a second end cap 612 disposed at opposing axial ends of the electrical sensor 600. The first and second end caps 610, 612 can be shaped as cylindrical, hollow tubes that each define an axial opening 614 to receive or discharge fluid flowing through the electrical sensor 600. In other embodiments, however, one of the first or second end caps 610, 612 may lack the opening 614 so that the electrical sensor 600 is effectively dead ended. The first and second end caps 610, 612 can include a radially raised lip or rim 616 located at the end opposite the opening 614. The first and second end caps 610, 612 preferably are made from a non-conductive, rigid material such as polycarbonate plastic or the like.

To interconnect the axially spaced first and second end caps 610, 612, the tubular electronic fabric probe 602 may have a length corresponding to the axial distance between the first and second end caps. The electronic fabric probe 602 can include a non-conductive fabric layer 620 made from a thin, pliable or flexible material that is formed into the tubular sleeve that surrounds the fluid chamber 604. Suitable materials for the non-conductive fabric layer include matted or woven fabrics or, more preferably, synthetic sheets or films. In a preferred embodiment, the non-conductive fabric layer 620 can be made from or include elastic materials to provide elasticity and resiliency and may be fluid impermeable to retain fluids in the flow chamber 604. The non-conductive fabric layer 620 can be initially formed as a thin, planner sheet of material that is rolled about the axis line 606 and sealed to form the tubular electronic fabric probe 602. Disposed at opposing axial ends can be a first elastic ring 622 and a second elastic ring 624. When installed on the first and second end caps 610, 612, the first and second elastic rings 622, 624 can be received over the corresponding rims 616 on the end caps 610, 612 to secure the electronic fabric probe 602 in place. The diameter of the first and second elastic rings 622, 624 can be slightly smaller than the rims 616 so they elastically compress about the rims to further secure the electronic fabric probe 602 in place.

To conduct or sense electricity in the electronic fabric probe 602, a plurality of electrode conductors 630 can be attached to the interior of the non-conductive fabric layer 620. Specifically, the electrode conductors 630 can be formed as long strips, tapes, or wires of conductive material that extend lengthwise and parallel with the axis line 606. Preferably, the electrode conductors 630 can extend at least coextensively between the first and second elastic rings 622, 624. Furthermore, the electrode conductors 630 can be arranged in a first conductor group 632 and a second conductor group 634 on opposing radial sides along the interior of the non-conductive fabric layer 620. Hence, the first conductor group 632 and the second conductor group 634 are physically and electrically separated from each other by the fluid chamber 604. Each of the first and second conductor groups 632, 634 correspond to a distinct radial or symmetrical half of the electronic fabric probe 602.

In an embodiment, to electrically communicate with the plurality of electrode conductors 630, the tail ends of the electrode conductors 630 disposed proximate to the elastic rings 622, 624 can contact corresponding contact pads 636 disposed on the exterior of the first and second end caps 610, 612. The contact pads 636 can be made of conductive material plated to the first and second end caps 610, 612 proximate the rims 616 and may extend axially away from the rims a short distance so they are partially exposed beyond the first and second elastic rings 622, 624. Hence, the contact pads 636 provide an accessible area in which electrical connection can occur between the electrode conductors 630 disposed inside the non-conductive fabric layer 620 and contacts or clips that may be used to connect the electrical sensor 600 to a medical device. Further, one contact pad 636 may be associated with the electrode conductors 630 of the first conductor group 632 and a second contact pad 636 can be associated with the conductors of the second conductor group 634 so the first and second conductor groups can be electrically connected to separate portions of the electrical circuit associated with the medical device.

By suspending the electronic fabric probe 602 between the first and second end caps 610, 612 of the rigid support body 604, the foregoing arrangement enables the electrical sensor 600 to be responsive to changes in fluid pressure of the fluid passing through the electrical sensor 600. Specifically, arrangement of electrode conductors 630 into the first and second conductor groups 632, 634 enables the electronic fabric probe 602 to measure changes in pressure in terms of corresponding changes with respect to an electrical characteristic of the electrical sensor, for example, the capacitance occurring between the plurality of electrode conductors 630 in the first conductor group 632 and the plurality of electrode conductors in the second conductor group 634. Because the electrode conductors 630 in the first conductor group 632 and the second conductor group 634 are arranged to oppose each other, and if the internal diameter of the electronic fabric probe 602 is small enough, an electromagnetic field and a resulting capacitive charge can build up between the first conductor group and the second conductor group when an electrical current is applied. For example, an electrical circuit conducting current such as direct current (DC) can be applied to the electrode conductors of the first conductor group 632 and the second conductor group 634 through the contact pads 636 on the rigid support body 604. Because they are electrically separated by the fluid chamber 604 and any fluid contained therein, the first conductor group 632 and the second conductor group 634 can function similarly to the opposing plates or terminals of a capacitor and can maintain an electrical charge between them. For example, the first conductor group 632 may be maintained at a negative charge and the second conductor group 634 at a positive charge resulting in a measurable capacitance in the electronic fabric probe 602.

The electrical charge can be measured in terms of the capacitance between the first conductor group 632 and the second conductor group 634 and may be a function of the voltage and/or current applied to the first and second conductor groups and the distance between them. The distance or separation between the first and second conductor groups 632, 634 corresponds to the diameter of the fluid chamber 604. Because the fluid chamber 604 is defined in part by the non-conductive fabric layer 620, which as described above may have an elastic or flexible characteristic, its diameter can change, for example, under the influence of fluid pressure inside the fluid chamber 604.

Referring to FIG. 11, there is illustrated an embodiment of the electrical sensor 600 when the fluid pressure inside the fluid chamber 604 is greater than the corresponding pressure externally surrounding the electronic fabric probe 602. Under this condition, the fluid pressure causes the non-conductive fabric layer 620 to expand radially outwardly increasing the diameter of the fluid chamber 604 changing the proximity and moving the electrode conductors of the first conductor group 632 apart from the electrode conductors of the second conductor group 634. The increased separation between the electrode conductors 630 results in a change of the capacitive charge and/or the electric field in the electronic fabric probe 602 that can be measured by a meter in the associated electrical circuit. If the fluid pressure were to decrease in the fluid chamber 604 relative to the exterior, the first and second conductor groups 632, 634 would move together resulting in another measureable change in capacitance. In this embodiment, either the first conductor group 632 or second conductor group 634 may function as a reference by providing the other conductor group with a second conductive element to electromagnetically interact with as the proximity between the groups changes.

Measuring change in capacitance by changing the proximity of the electrode conductors enables the electrical sensor 600 to measure the changes in fluid pressure arising from various causes. For example, change in fluid pressure may result from changes in velocity of the fluid, changes in its composition, or the like. Additionally, changes in the fluid pressure may reflect displacement of some other part of the fluid circuit that can be recognized by the electrical sensor. It can be appreciated that other configurations for an electrical sensor that measures changes in fluid pressure by monitoring the dimensional proximity and electrical capacitance between two or more groups of opposing conductors embedded in an electronic fabric probe are possible. For example, the fluid pressure may be directed externally of the electrical sensor 600 to move the first and second conductors groups towards each other, or the electrode conductors may be embedded in opposing fabric membranes arranged on either side of a fluid chamber that move together or diverge in response to pressure changes. Further, one group of electrode conductors may be disposed in a fixed position while the other group is attached to the flexible electronic fabric probe that enables relative displacement of the conductors.

Figure 12:
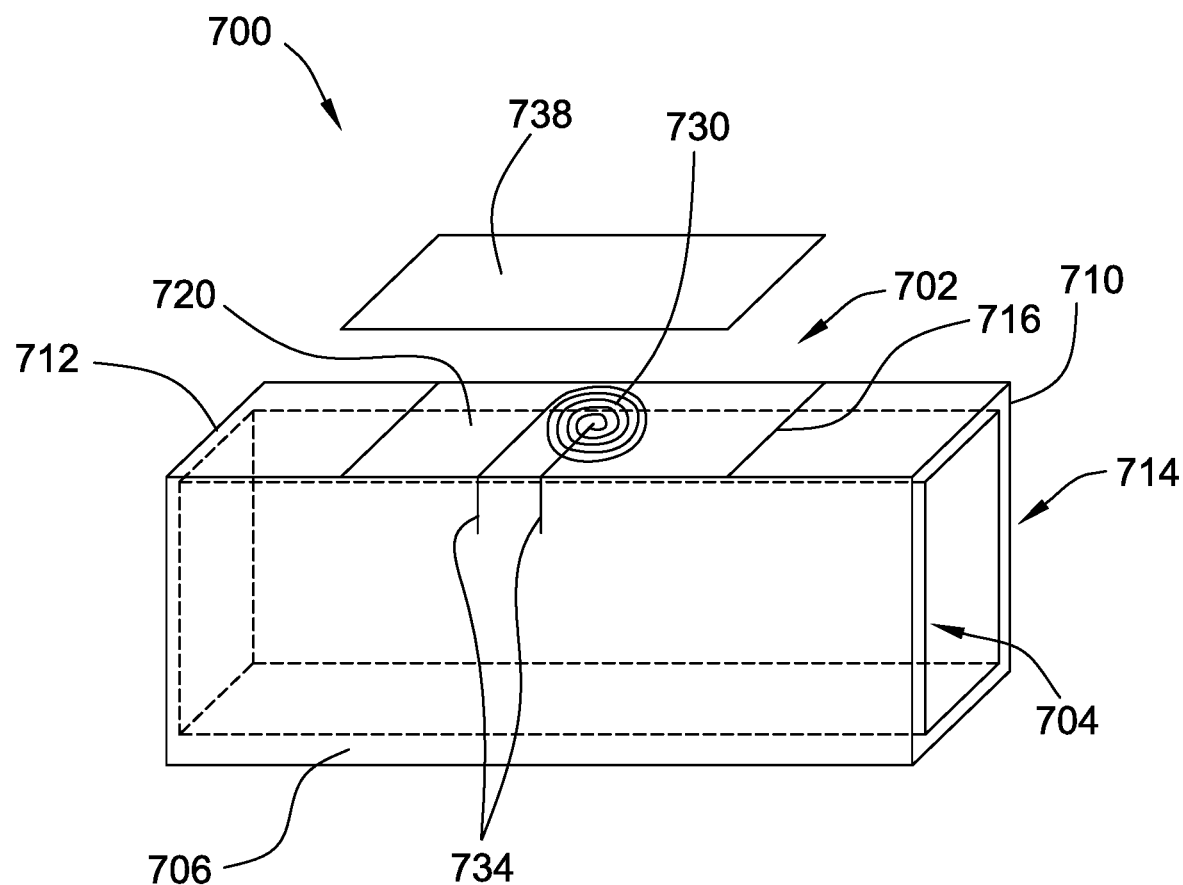
FIG. 12 is a perspective schematic of an embodiment of the electrical sensor having the electronic fabric probe arranged to measure fluid pressure via the inductance associated with the electrical sensor.

In addition to utilizing capacitance to measure pressure or proximity changes, referring to FIG. 12, there is illustrated an embodiment of an electrical sensor 700 having an electronic fabric probe 702 that may utilize inductance. The electronic fabric probe 702 is supported by and exposed to a fluid chamber 704 defined in a rigid support body 706. In this embodiment, the rigid support body 706 may be configured as a square or rectangular hollow tube extending between a first end 710 and an opposing second end 712, each of which define an opening 714 to receive and discharge fluid through the fluid chamber 704. Accordingly, the electrical sensor 700 has an axial flow-through configuration, but in other embodiments the sensor may be dead-ended. The rigid support body 706 can be made from a non-conductive material such as polycarbonate plastic.

To accommodate the electronic fabric probe 702 in relation to the fluid chamber 704, the rigid support body 706 can have an aperture 716 or a rectangular window disposed through its body and located between the first and second ends 710, 712. The electronic fabric probe 702 can have a corresponding rectangular shape and can be attached to cover the aperture 716 by any suitable method including adhesives or sonic welding. To support the electrode conductors and provide a flexible or pliable characteristic, the electronic fabric probe 702 can include a non-conductive fabric layer 720 of any of the aforementioned materials, which preferably may include elastic materials and is fluid impermeable. The non-conductive fabric layer 720 is a planar sheet of the flexible material and can be cut in the shape of the aperture 716 to lie over or enclose the aperture.

To sensitize the electronic fabric probe 720 to an electromagnetic field, a conductive element or electrode conductor 730 embedded in the non-conductive fabric layer 720 may be configured as a thin strip or wire that is wound into a coil. In particular, the electrode conductor 730 can include a plurality of wound spirals that start and terminate with leads 734 that may be accessibly exposed on the exterior of the rigid support body 706. Application of an electric current to the leads 734 causes current to flow in the coil which generates a magnetic field around the electrode conductor 730 according to the principle of inductance. Further, if the current changes or reverses direction, e.g., an alternating current (AC) is applied to the leads 734 of the electrode conductor 730, the generated magnetic field will likewise change directions and/or magnitude. The magnetic field can permeate through the non-conductive fabric layer 720. In various embodiments, the coil of the electrode conductor 730 may be wound about a conductive core or the like to increase the strength of the generated magnetic field.

To responsively interact with the generated magnetic field, a second conductive element 738, such as a conductive metal plate, can be disposed in proximity to the electrode conductor 730 to serve as a reference. The second conductive element 738 can be parallel to and generally coextensive with the electronic fabric probe 702 and can be secured in a fixed location at, for example, a few millimeters from the probe to interact with the magnetic field. The magnetic field can cause an electromagnetic reaction in the second conductive element that can result in the induction of a counter electrical current or eddy currents in the second conductive element. Moreover, if the generated magnetic field varies with the application of AC in the electrode conductor 730, the induced currents or eddy currents in the second electrical element 738 or reference will likewise change. The changing eddy currents can create changes in the inductance of the coil-like first electrode conductor 730, which can be measured by an appropriate meter or circuit connected to the leads 734.

Because the electronic fabric probe 702 is exposed to the flow chamber 704 through the aperture 716, the non-conductive fabric layer 720 can deflect with changes or variations of the fluid pressure in the flow chamber. Accordingly, if the pressure increases, the non-conductive fabric layer 720 can be displaced toward the second conductive element 738 and, if the pressure decreases, it can be retracted from the second conductive element. Displacement of the non-conductive fabric layer 720 therefore changes the proximity of the electrode conductor 730 and the second conductive element 738, or reference, with respect to each other in a manner that has a measureable effect on the inductance of the first electrode conductor 730. By calibrating the internal pressure in the fluid chamber 704, resulting displacement of the non-conductive fabric layer 720, and the change in inductance, the electrical sensor can indicate the pressure and/or flow rate of the fluid through the electrical sensor 700. In other embodiments, the arrangement of the electronic fabric probe 702, the flow chamber 704 and the rigid body defining the flow chamber can be different than as shown and described in FIG. 12 including having different flow paths and the like.

Sensor Identification and Authentication

Figure 13:
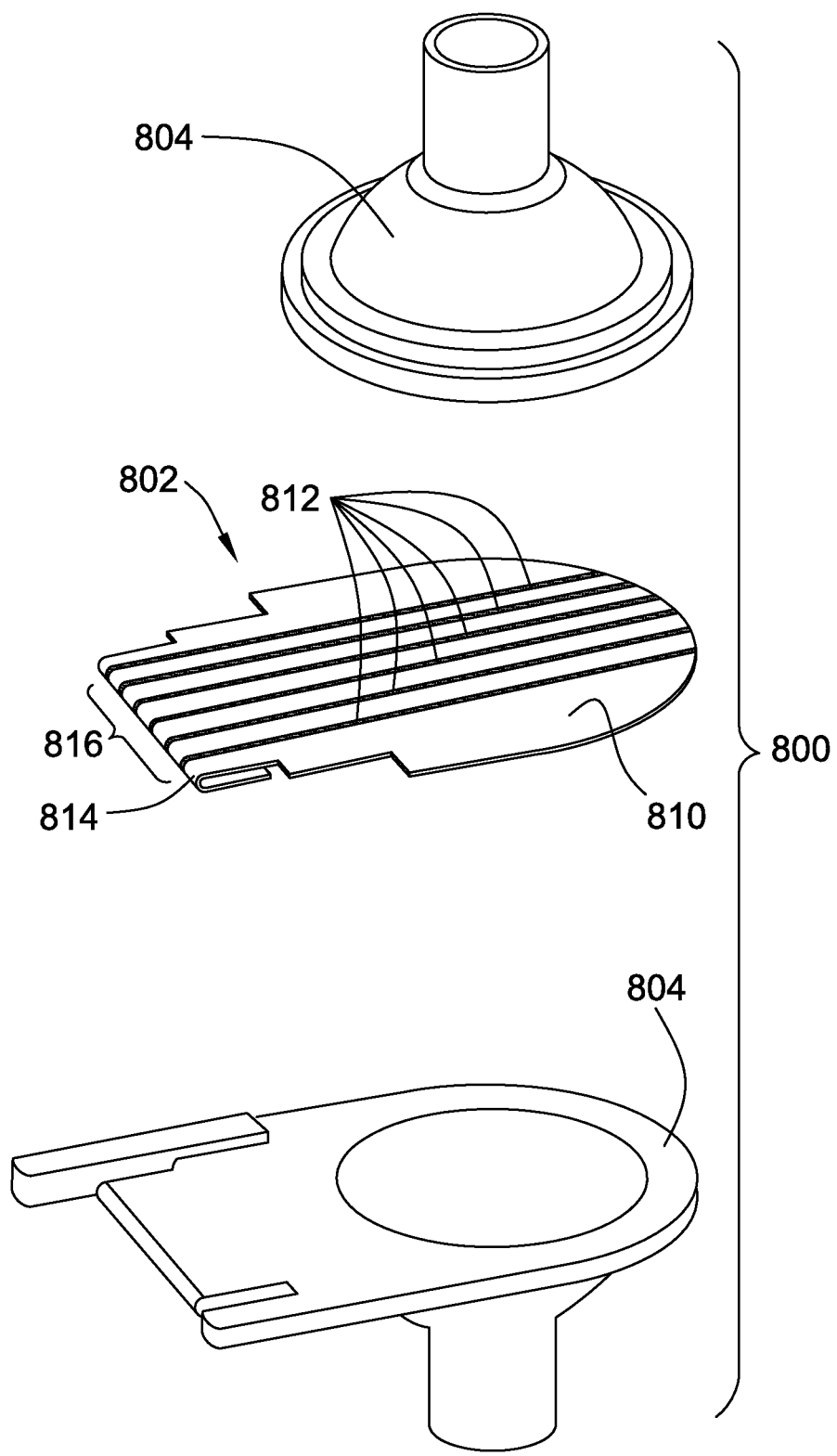
FIG. 13 is a perspective assembly view of an embodiment of the electrical sensor including an electronic fabric probe having a plurality of electrical conductors arranged to provide a visual indication to identify or authenticate the electronic fabric probe.

In further embodiments, the electronic fabric probe can be configured to provide identification information and authentication features to ensure the electrical sensor is correctly installed in the medical device. Referring to FIG. 13, for example, there is illustrated an embodiment of an electronic fabric probe 802 that can be installed in an enclosure 804 for an electrical sensor 800 to sense fluid properties. The electronic fabric probe 802 includes a non-conductive fabric layer 810 in which a plurality of electrode conductors 812 are embedded. The non-conductive fabric layer 810 can be made from any of the foregoing fluid permeable or impermeable materials and can have flexible or pliable characteristics to facilitate installation into the enclosure 804. The non-conductive fabric layer 810 can have any suitable shape depending upon the application including, in the illustrated embodiment, being cut or stamped as a tongue-shaped piece of fabric that includes at least one side edge 814. In this embodiment, the plurality of electrode conductors 812 can be a series of elongated, conductive strips or wires extending across the non-conductive fabric layer 810 and generally arranged in parallel with each other. The plurality of electrode conductors 812 can be arranged to sense conductivity of a fluid directed across the fabric probe 802, although in other embodiments the electrode conductors 812 can be arranged to sense other fluid characteristics such as pressure or temperature. In the present embodiment, the visual color of the plurality of electrode conductors 812 is preferably distinct from the color of the non-conductive fabric layer 810 so those elements are visually distinguishable.

To enable the plurality of electrode conductors 812 to make electrical contact with corresponding leads or contacts disposed exteriorly of the electrical sensor 800, the electrode conductors may include terminal portions 816 that terminate at and are disposed along the side edge 814 of the non-conductive fabric layer 802. Accordingly, when the fabric probe 802 is accommodated in an enclosure 804 of the electrical sensor 800, the side edge 814 and the terminal portions 816 of the electrode conductors 804 are accessible outside of the enclosure. In an embodiment, to identify and communicate information or data about the electronic fabric probe 802 and/or the electrical sensor 800, the terminal portions 816 of the plurality of electrode conductors 812 can be arranged to form a recognizable pattern used to convey identification information. In particular, because the terminal portions 816 are arranged in parallel and distinctly spaced apart along the exposed side edge 814, they can provide a type of readable barcode based on their spacing, thicknesses, color and/or contrast, etc. An optical scanner or machine reader can be used to scan the terminal portions 816 and the exposed strips of the non-conductive fabric layer 810 there between and interpret their arrangement in a manner that conveys information about the electronic fabric probe 802 and/or electrical sensor 800. The information can regard the make and model of the sensor, its electrical or fluid characteristics or properties, its intended installation information, etc. In another embodiment, the recognizable pattern created by the exposed terminals may represent other information, such as a visible indication of left or right for mating the electrical sensor with a mating connector.

Figure 14:
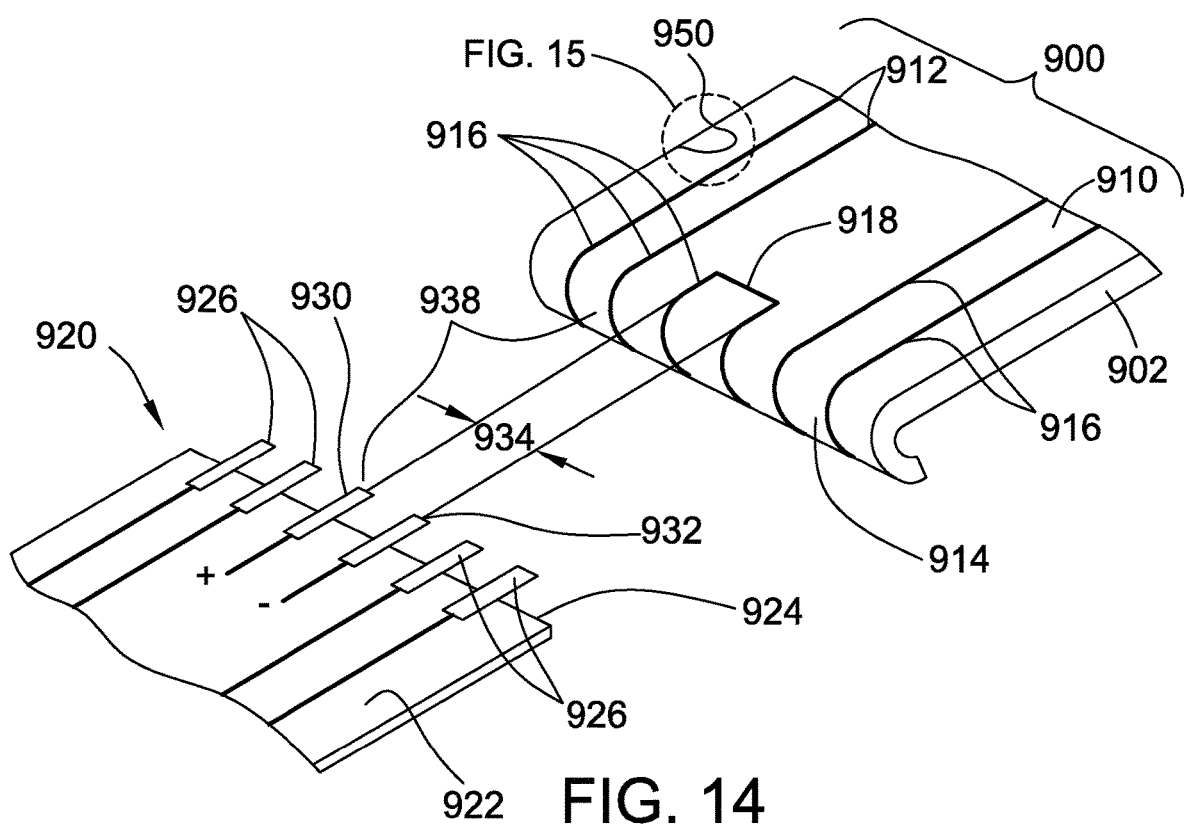
FIG. 14 is a perspective assembly view of an embodiment of an electronic fabric probe arranged to mate with an electrical connector and including a dedicated electrode conductor verify or authenticate the mating electrical connector.

Referring to FIG. 14, there is illustrated another embodiment in which the electronic fabric probe 902 of an electrical sensor 900 is configured to provide an identification and authentication feature. The electronic fabric probe 902 can include a non-conductive fabric layer 910 having planar, pliable characteristics with a plurality of electrode conductors 912 embedded into the non-conductive fabric layer 910. Any of the foregoing materials and configurations described herein are suitable for the non-conductive fabric layer 910 and the plurality of electrode conductors 912. Similarly, the electrode conductors 912 can be elongated strips or wires arranged in parallel and which include terminal portions 916 disposed perpendicularly along a side edge 914 of the non-conductive fabric layer 910 to enable electrical contact with a mating electrical connector of a corresponding electrical circuit.

In FIG. 14, the mating electrical connector 920 operatively associated with the electrical sensor 900 can include a planar board 922 such as a printed circuit board or the like with circuit traces disposed thereon and configured to establish a board-to-board connection with the electronic fabric probe 902. The planar board 922 can include a leading edge 924 oriented toward the side edge 914 of the fabric probe 902 and which includes a plurality of aligned conductive contacts 926, which may be pins, prongs, or springs projecting perpendicularly there from or otherwise accessible thereon and that may be in electrical communication with traces on the planar board 922. The plurality of conductive connector contacts 926 can be spaced apart and arranged to complementarily and dimensionally correspond to the plurality of terminal portions 916 of the electrode conductors 912 along the side edge 914 of the electronic fabric probe 902. When the electronic fabric probe 902 and the electrical connector 920 are moved together, the terminal portions 916 can make sliding contact with the projecting connector contacts 926 to establish electrical communication between the elements.

To authentic the electrical sensor 900, in an embodiment, the mating electrical connector 920 can include at least a first connector contact 930 and a second connector contact 932 arranged on the leading edge 924 to contact a special purpose or dedicated electrode conductor 918 on the electronic fabric probe 902. The first and second connector contacts 930, 932 can be spaced apart from each other a specific distance 934 that corresponds in dimension and location to the distance between the terminal portions 916 of the dedicated electrode conductor 918. The first and second connector contacts 930, 932 and the terminal portions 916 of the dedicated electrode conductor 918 are further correspondingly aligned with each other with respect to the side edge 914 of the probe and leading edge 924 of the board 922 to ensure they make sliding contact with each other. The first and second connector contacts 930, 932 can be electrically coupled via traces on the planar board 922 with a circuit or power source and the dedicated electrode conductor 918 can be configured to complete or close the electrical circuit, thereby forming an authentication or verification circuit 938. Hence, the contact patterns between the first and second conductor contacts 930, 932 are matched to the dedicated electrode conductor 918 on the electronic fabric probe 902. The location and spacing between the first and second connector contacts 930, 932 and the terminal leads 916 of the dedicated electrode conductor 918 can be particularized for different electrical sensors 900 to verify correct connection of the electrical sensor and the mating electrical connector 920. If the first and second conductor contacts 930, 932 and the dedicated electrode conductor do not align 918, the verification circuit 938 will not be completed. The verification circuit 938 may be connected with a power switch, warning alarm or other measure to prevent unintended use of the electrical sensor. In other embodiments, the dedicated electrode conductor 918 can include multiple electrode conductors 912 that may also serve as part of the sense or excitations functions of the electrical sensor.

Figure 15:
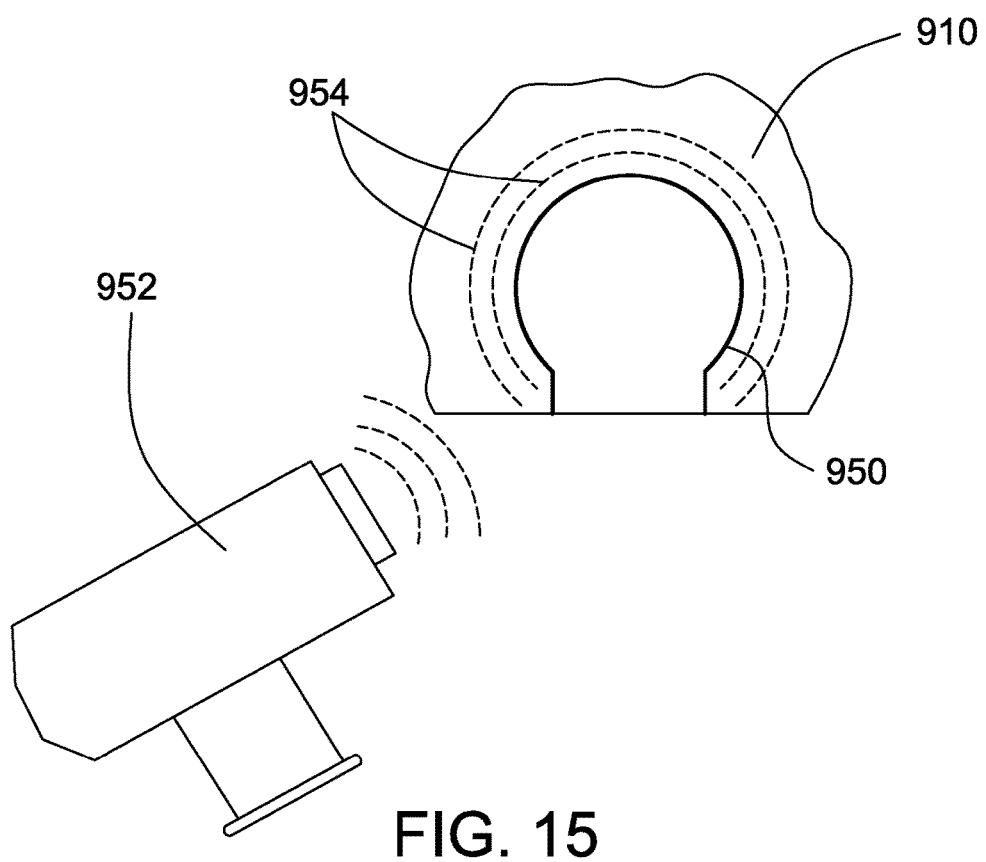
FIG. 15 is a detailed view of the area indicated in FIG. 14 illustrating another dedicated electrical conductor arranged as an antenna to transmit radio signals to identify the electronic fabric probe.

Referring to FIGS. 14 and 15, in a further embodiment, the electronic fabric probe 900 can include a second dedicated electrode conductor 950 or set of electrode conductors embedded in the non-conductive fabric layer 910 that is configured as an antenna to transmit or convey information regarding the electronic fabric probe 900. The second dedicated electrode conductor 950 in the form of an antenna can be made from a thin strip or wire of conductive material bent or shaped into a pattern to function as a radio frequency identification ("RFID") tag. In an embodiment, the second dedicated electrode conductor 950 can be configured as a passive RFID that responds to an applied energy field as may be emitted from a radio frequency scanner 952 placed in proximity to and directed toward the electronic fabric probe 902. When an energy field of the correct frequency and/or wavelength is applied, small responsive currents may be generated in and conducted through the second dedicated electrode conductor 950. Further, those currents can generate a responsive electromagnetic field of radio waves in the form of a radio signal 954 that can be received by the radio frequency scanner 952 or another scanner. The transmitted radio signal 954 can be unique to the second dedicated electrode conductor 950, for example, based on the shape of the conductor, its material properties, or other characteristics. The radio signal 954 can convey or represent information regarding the electronic fabric probe 900 in which the second dedicated electrode conductor 950 is embedded. An advantage of utilizing RFID technology is the second dedicated electrode conductor 950 need not be located in an exposed location, for example, along the side edge 914, since radio waves can permeate through many materials that may used for the probe enclosure or the like. In embodiments in which electricity is applied to the first electrode conductors 912 of the electronic fabric probe 902, the second dedicated electrode conductor 950 may be configured as an active device receiving power from the applied electricity to the first electrode conductor 912 to emit a radio signal without the need for an initiating or stimulating field.

Shielded Sensors

Figure 16:
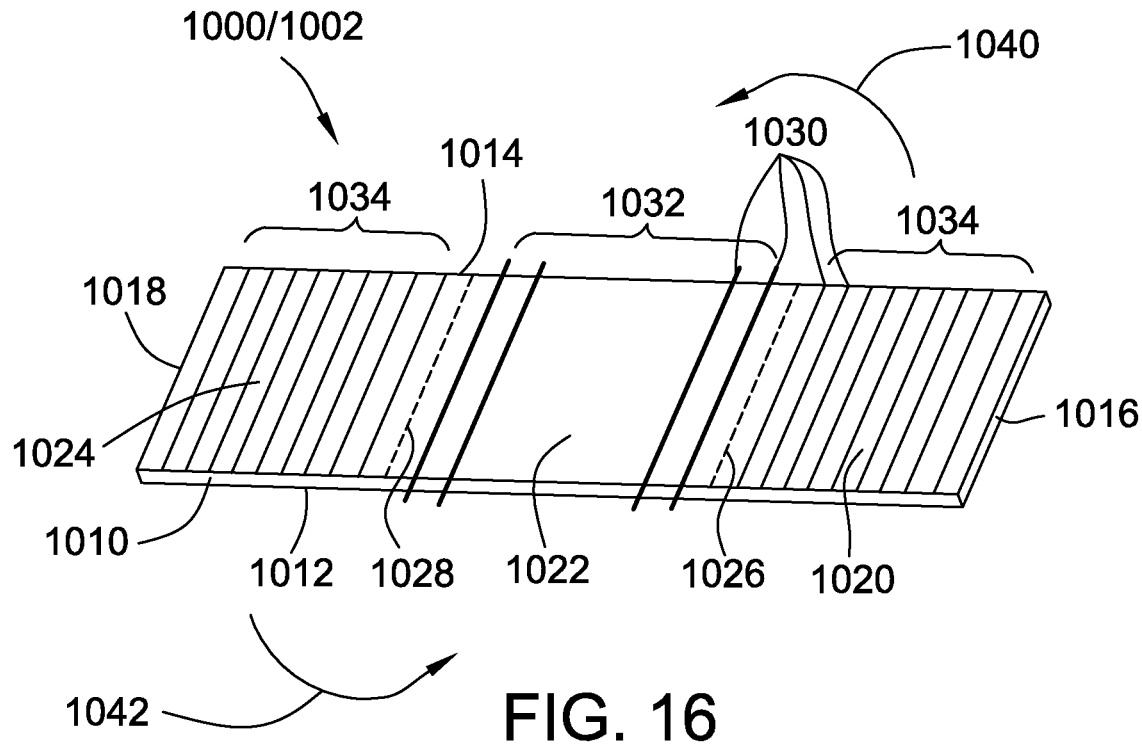
FIG. 16 is a perspective view of another embodiment of an electronic fabric probe having an active first conductor group and a passive second conductor group for providing electromagnetic shielding for the electrical sensor.
Figure 17:
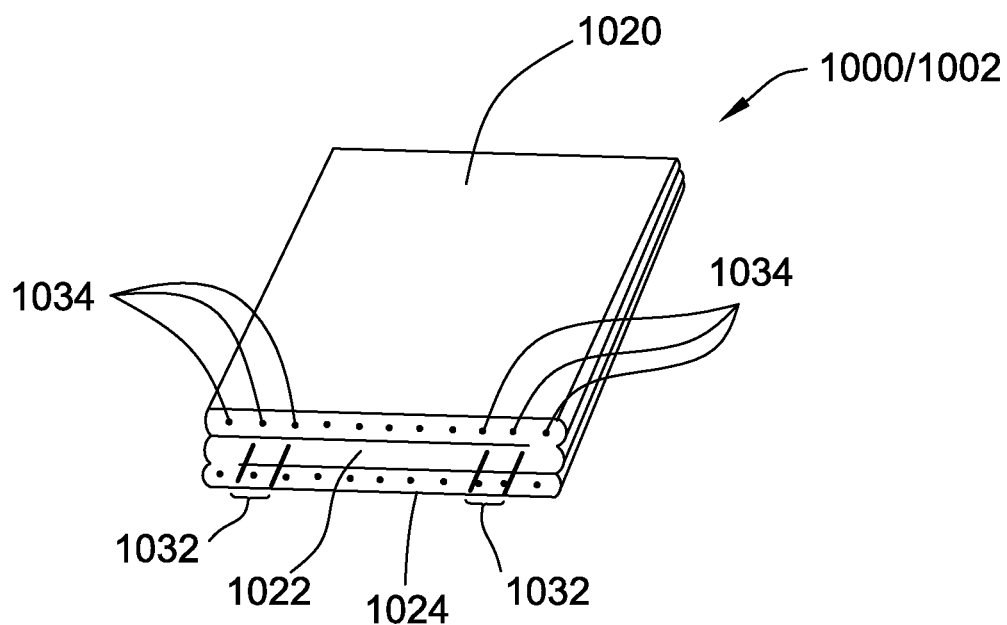
FIG. 17 is a perspective view of the electronic fabric probe of FIG. 16 as folded and assembled so the passive second conductor group shields the active first conductor group.

In another aspect, the electronic fabric probe for the electrical sensor can be configured to provide electromagnetic shielding to the electrical conductors that may be embedded in the non-conductive fabric layer. Referring to FIGS. 16 and 17, there is illustrated an embodiment for making an electrical sensor 1000 having a shielded electronic fabric probe 1002. The electronic fabric probe 1002 includes a non-conductive fabric layer 1010 that may be a planar, rectangular strip of material such as described above. Preferably, the material is relatively thin, has a flexible or pliable characteristic allowing it to be creased or folded about itself, and may be fluid permeable. Any of the aforementioned non-conductive fabric materials can be used for the non-conductive fabric layer 1010. To define the rectangular shape, the non-conductive fabric layer 1010 can include a first side edge 1012 and a parallel second side edge 1014 that define its width and a first end edge 1014 and a second end edge 1016 that define its length. As explained further below, the embodiment of the non-conductive fabric layer 1010 may further be arranged into a first section 1020, a second section 1022, and a third section 1024 with respect to its lengthwise extension such that the sections are generally quadrilateral. The first, second, and third sections 1020, 1022, 1024 can have generally equal dimensions and may be separated by a first fold line 1026 and a second fold line 1028 (indicated in dashed lines) that are perpendicular to the first and second side edges 1012, 1014 and parallel to the first and second end edges 1016, 1018.

In this embodiment, the electrode conductors 1030 embedded into the non-conductive fabric layer 1010 can be arranged into a first conductor group 1032 and a second conductor group 1034. The first conductor group 1032 can be embedded in the middle second section 1022 of the non-conductive fabric layer 1010 extending across its width between the first and second side edges 1012, 1014. The first conductor group 1032 furthermore can be parallel to and constrained by the first fold line 1026 and second fold line 1028. The fold lines 1026, 1028 may be representative only or may be formed as creases, indentations, or perforations in the non-conductive fabric layer 1010. The electrode conductors 1030 of the first conductor group 1032 can again be thin parallel strips or wires of conductive material arranged apart from each other to maintain electrical isolation. In the illustrated embodiment, the electrode conductors 1030 of the first conductor group 1032 can be designated as active electrodes such as excitation or sense electrodes, meaning the conductors of the first conductor group 1032 are configured or intended for connection to appropriate meters or power sources. To make electrical contact with connectors or circuit elements, the electrode conductors 1030 of the first conductor group 1032 may protrude or extend slightly beyond the first side edge 1014 and second side edge 1016 of the non-conductive fabric layer 1010.

To provide shielding for the active electrodes in the first conductor group 1032, the second conductor group 134 can be embedded in the first and third sections 1020, 1024 of the non-conductive fabric layer 1010. Similar to the first conductor group 1032, the electrode conductors 1030 of the second conductor group 1034 can be parallel to each other and the fold lines 1026, 1028 so they extend across the width of the non-conductive fabric layer 1010 perpendicular to the first and second side edges 1012, 1014; however, in other embodiments, the electrode conductors 1030 of the second conductor group 1034 may have different orientations or arraignments such as a diagonal arrangement, an interconnected grid, or the like. Moreover, the individual electrode conductors 1030 of the second conductor group 1034 can have different dimensions or thicknesses with respect to the electrode conductors 1030 in the first conductor group 1032. The electrode conductors 1030 of the second conductor group 1034 can be designated as passive electrodes, meaning they are not configured to electrically communicate with another circuit. As passive electrodes, the electrode conductors 1030 of the second conductor group 134 remain electrically isolated from the other circuits or electrical connectors that may mate to the electrical sensor 1000.

To assemble the electrical sensor 1000, the first section 1020 of the non-conductive fabric layer 1010 can be folded parallel about the first fold line 1026 adjacent to and over the second section 1022 as indicated by arrow 1040. The third section 1024 can be folded with respect to the second fold line 1028 also adjacent to and underneath the middle section 1024 as indicated by arrow 1042. The middle second section 1022 is thereby sandwiched between the opposing first section 1020 and third section 1024 and the first and second electrode groups are disposed in three separate and parallel planes. When installed in an appropriate electrical sensor, fluid can be directed through the adjacent first, second and third sections 1020, 1022, and 1024 to encounter the electrode conductors 1030 therein. Because the passive second conductor group 1034 is included in the first and third sections 1020, 1024, they can isolate the active first conductor group 1032 in the second section 1022 of the non-conductive fabric layer 1010 from electromagnetic interference.

For example, an applied external electromagnetic field is neutralized by induced currents in the passive second conductor group 1034 surrounding the active first conductor group 1032 such that the electromagnetic field will not interfere with the first conductor group due to the faraday effect. To facilitate shielding, the electrode conductors 1030 of the second conductor group 1034 preferably extend across the fully width of the non-conductive fabric layer 1010 between the first and second side edges 1012, 1014. In different embodiments, the electrode conductors of the passive second conductor group 1034 disposed in the first and third sections 1020, 1024 may be isolated or they may be electrically interconnected with each other to facilitate shielding of the active first conductor group 1032 disposed there between. In addition to shielding the active first conductor group 1032, the passive second conductor group 1034 can absorb electromagnetic waves emitted from the first conductor group to avoid interfering with other electrical components. In an embodiment, the spacing between individual elements of the second conductor group 1034 can be selected to sensitize the electronic fabric probe to specific wavelengths of electromagnetic interference. In an embodiment, the second conductor group 1034 may be interconnected to provide a closed circuit, or may be connected to an electrical ground to discharge any induced currents. In further embodiments, additional folds or different folding arrangements of the active and passive electrodes may be utilized.

Diagnostic Circuit

Figure 18:
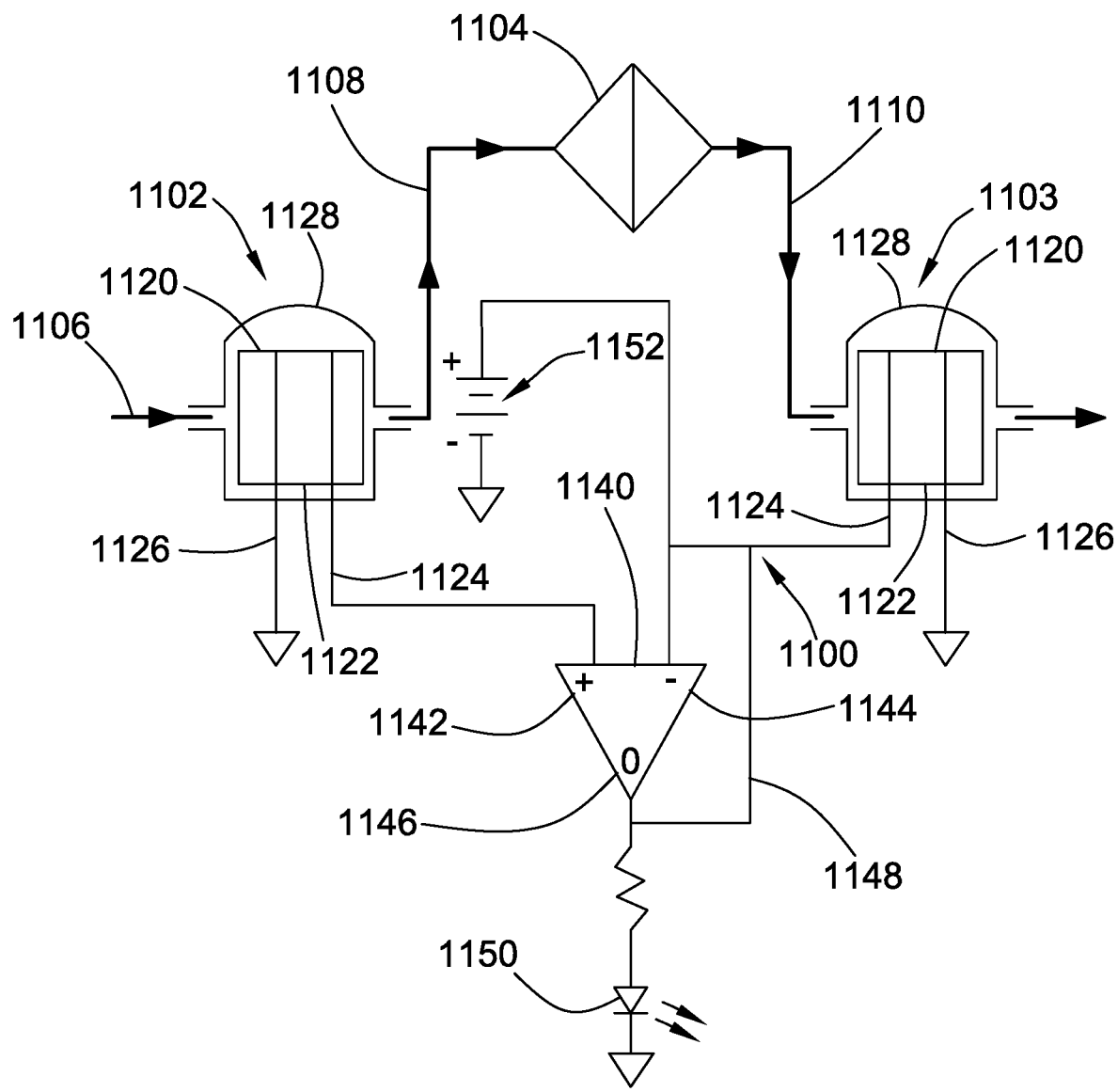
FIG. 18 is a schematic diagram of an electrical circuit using electrical sensors having electronic fabric probe arranged to monitor a filter in fluid circuit.

As indicated above, an electronic sensor utilizing electronic fabric probes can be used for internal diagnostics with fluid circuits in medical devices. Referring to FIG. 18, there is illustrated an embodiment of an electrical circuit 1100 (illustrated in thin lines) using a first electrical sensor 1102 and second electrical sensor 1103 of the type described herein to monitor a fluid operation such as, for example, the effectiveness of a filter 1104 disposed in a fluid circuit 1106 (illustrated in thick lines). The filter 1104 can be any suitable type of fluid filter and is disposed in the fluid circuit 1106 in a manner that separates the circuit into an upstream branch 1108 and a downstream branch 1110. Fluid flows from the upstream branch 1108 to the filter 1104 that removes contaminates and that discharges the purified fluid to the downstream branch 1110. Pumps, such as peristaltic tube pumps or the like, can be disposed in the fluid circuit 1106 to direct fluid there through. In an embodiment, the fluid directed to the filter 1104 by the fluid circuit 1106 can be a dialysis fluid including fresh or used dialysate. In addition to utilizing the electrical circuit 1100 to monitor fluid filtration, other embodiments of the electrical circuit may be used to monitor other fluid operations such as measuring the introduction of chemicals or additives to the fluid, fluid ionization, etc.

To monitor the effectiveness of the filter 1104 in removing contaminants from the fluid, a first electrical sensor 1102 is disposed in the upstream branch 1108 before the filter 104 or other operation and the second electrical sensor 1103 is disposed in the downstream branch 1110 after the filter or other operation. The first and second electrical sensors 1102, 1103 can include electronic fabric probes 1120 having any of the foregoing constructions. The electronic fabric probe 1120 can include a non-conductive fabric layer 1122 of flexible or pliable, non-conductive fabric material provided as a thin, planar sheet. To function as electrodes, a plurality of electrode conductors including at least a first electrode conductor 1124 and a second electrode conductor 1126 can be embedded in the non-conductive fabric layer 1122. The electrode conductors 1124, 1126 can be narrow conductive strips or wires woven, stitched or adhered into the non-conductive fabric layer in a parallel manner. In an embodiment, to support the electronic fabric probes 1120 and establish fluid communication with fluid in the circuit 1106, the probes can be accommodated in a non-conductive probe enclosure 1128. The electronic fabric probes 1120 can be designed as the flow-over or the flow-through types depending on the configuration of the probe enclosure 1128

In operation, if the filter 1104 is functioning, fluid in the upstream branch 1108 should be relatively more conductive than fluid in the downstream branch 1110 because the filter 1104 should remove charge carriers and conductive ions that may be equated with unwanted contaminants. The ions can include calcium $Ca^+$, chlorine $Cl^-$ or any other undesired ions. The filtered fluid in the downstream branch 1110 will therefore be relatively non-conductive if the filter is properly functioning. The electrical circuit 1100 compares electrical characteristics between the fluid as measured by the first electrical sensor 1102 in the upstream branch 1108 and by the second electrical sensor 1103 in the downstream branch 1110. In particular, the electrical circuit 1100 compares the voltage differential between the first and second electrical sensors 1102, 1103.

To compare the voltage differential, the electric circuit 1100 includes a comparator 1140 disposed in electrical communication with the first and second electrical sensors 1102, 1103. The comparator 1140 can be an electronic device such as a differential amplifier or similar integrated circuit device. The comparator 1140 can include a first input 1142 or positive input and a second input 1144 or negative input that communicate with a common output 1146. The first input 1142 can be electrically connected to the first electrode conductors 1124 of the first and second electrical sensors 1102, 1103, and the second electrode conductors 1126 can be connected, for example, to another portion of the electrical circuit to communicate with conductivity meters or the like. The common output 1146 of the comparator 1140 can be connected to an indicator element such as a light-emitting diode ("LED") 1150, an audio alarm, or a similar warning device. To facilitate operational control of the comparator 1140, a feedback loop may connect the output 1146 to the second input 1144. The comparator 1140 can obey the following electrical convention based on the signals applied to its first and second inputs 1142, 1144:

If $V^+(1142) > V^-(1144)$, then $V_{out}(1146) = 1$; (Eqn. 3)

If $V^+(1142) < V^-(1144)$, then $V_{out}(1146) = 0$. (Eqn. 4)

To apply voltage to the electrical circuit 1100, a battery 1152 is connected by its positive terminal to the second input 1124 and also to the first electrode conductor 1124 in the second electrical sensor 1103. If the fluid in the downstream electrical sensor 1103 is sufficiently non-conductive, the signal (i.e. voltage) applied the second input 1144 is comparatively high with respect to the first input 1142 and the output 1126 is zero per Eqn. 4. If the filter 1104 becomes saturated or fails, fluid in the second electrical sensor 1103 becomes conductive relative to the first electrical sensor 1102. Current from the battery 1152 can pass from the first electrode conductor 1124 in the downstream electrical sensor 103 to the second electrode conductor 1126 causing the signal (i.e. voltage) on the second input 1144 to fall compared to the first input 1142. The output 1146 therefore goes high per Eqn. 3 causing the LED 1150 to light to indicate the filter 1104 requires replacement. Hence, the foregoing electrical circuit 1100 monitors the usefulness of a filter 1104 or other operation that may be disposed in a fluid circuit 1106 of a medical device using low-cost electronic fabric probes 1120.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system, comprising:
   an electrical sensor, comprising:
      an enclosure defining a flow path for fluid;
      an electrical fabric probe disposed in the flow path, the electrical fabric probe including a non-conductive fabric layer and a plurality of conductors attached to the non-conductive fabric layer, the plurality of conductors including at least a first sense electrode, a second sense electrode, and a third sense electrode arranged to sense voltage between the first and second sense electrodes and between the second and third sense electrodes; and
      a port disposed upstream of the plurality of conductors for receiving a tracer or bolus and introducing the tracer or bolus into the flow path; and
   a controller configured to determine a flow rate of the fluid in the flow path based on changes in voltage sensed by the first, second and third sense electrodes corresponding to the tracer or bolus crossing over the first, second and third sense electrodes.

2. The system of claim 1, wherein the first, second and third sense electrodes are parallel to one another, and wherein the distance between the first and second sense electrodes is equal to the distance between the second and third sense electrodes.

3. The system of claim 1, further comprising a first excitation electrode and a second excitation electrode attached to the non-conductive fabric layer such that the first, second and third sense electrodes are disposed between the first and second excitation electrodes.

4. The system of claim 2, wherein the controller is further configured to perform a diagnostic operation on the electrical sensor by determining, while a fluid of consistent conductivity flows across the first, second and third sense electrodes, whether a measured voltage between the first and second sense electrodes differs from a measured voltage between the second and third sense electrodes by an amount greater than a tolerance threshold.

5. The system of claim 1, wherein the electrical sensor has a flow-over configuration and the non-conductive fabric layer of the electrical fabric probe has a planar shape.

6. A system, comprising:
   an electrical fabric probe defining an internal fluid chamber, wherein the electrical fabric probe includes a flexible non-conductive fabric layer, a first conductor attached to the flexible non-conductive fabric layer, and a second conductor attached to the flexible non-conductive fabric layer; and
   a controller configured to determine a change in fluid pressure based on a change in an electrical characteristic measured via the first and second conductors, wherein the change in the electrical characteristic is caused by a distance between the first and second conductors being increased due to fluid within the internal fluid chamber acting upon the flexible non-conductive fabric layer.

7. The system of claim 6, wherein the measured electrical characteristic is a capacitance between the first and second conductors.

8. The system of claim 6, wherein one out of the first and second conductors serves as a reference.

9. The system of claim 6, wherein the first and second conductors are arranged opposite to one another across the internal fluid chamber.

10. The system of claim 6, wherein the flexible non-conductive fabric layer is configured to expand outward due to fluid pressure from the fluid within the internal fluid chamber increasing, and wherein expansion of the flexible non-conductive fabric layer outward increases the distance between the first and second conductors.

11. The system of claim 10, wherein the electrical fabric probe has a hollow, tubular shape, and wherein the flexible non-conductive fabric layer is configured to expand radially outward due to fluid pressure from the fluid within the internal fluid chamber increasing.

12. A shielded electrical fabric sensor, comprising:
   a flexible non-conductive fabric layer; and
   a plurality of conductors attached to the flexible non-conductive fabric layer, wherein the plurality of conductors include a passive conductor group disposed in a first section of the flexible non-conductive fabric layer and an active conductor group disposed in a second section of the flexible non-conductive fabric layer;
   wherein the flexible non-conductive fabric layer is folded along a fold line between the first section and the second section such that the passive conductor group disposed in the first section is disposed over the active conductor group disposed in the second section.

13. The electrical fabric sensor of claim 12, wherein the plurality of conductors further include a passive conductor group disposed in a third section of the flexible non-conductive fabric layer;
   wherein the flexible non-conductive fabric layer is further folded along a fold line between the second section and the third section such that the passive conductor group disposed in the third section is disposed under the active conductor group disposed in the second section.

14. The electrical fabric sensor of claim 12, wherein the flexible non-conductive fabric layer being folded along the fold line between the first section and the second section causes a surface of the first section and a surface of the second section to be directly adjacent to one another.

15. The electrical fabric sensor of claim 12, wherein the flexible non-conductive fabric layer is fluid permeable.

* * * * *